US006344554B1

(12) United States Patent
Johnson et al.

(10) Patent No.: US 6,344,554 B1
(45) Date of Patent: Feb. 5, 2002

(54) **POLYNUCLEOTIDE SEQUENCES FROM *CANDIDA ALBICANS* ENCODING POLYPEPTIDES ASSOCIATED WITH FILAMENTOUS GROWTH**

(75) Inventors: Alexander D. Johnson; Burkhard Braun, both of San Francisco, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/165,239

(22) Filed: Oct. 1, 1998

Related U.S. Application Data

(60) Provisional application No. 60/068,065, filed on Dec. 18, 1997, and provisional application No. 60/061,058, filed on Oct. 2, 1997.

(51) Int. Cl.$^7$ .............................................. C07H 21/04

(52) U.S. Cl. ........................................ 536/24.32; 435/6

(58) Field of Search ........................... 536/24.32; 435/6

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,754,065 | A | 6/1988 | Levenson et al. |
| 4,800,159 | A | 1/1989 | Mullis et al. |
| 4,968,603 | A | 11/1990 | Slamon et al. |
| 5,124,426 | A | 6/1992 | Primeaux, II et al. |
| 5,436,142 | A | 7/1995 | Wigler et al. |
| 5,501,964 | A | 3/1996 | Wigler et al. |
| 5,565,340 | A | 10/1996 | Chenchik et al. |
| 5,580,736 | A | 12/1996 | Brent et al. |

FOREIGN PATENT DOCUMENTS

| | | |
|---|---|---|
| WO | WO 94/00601 | 1/1994 |
| WO | WO 94/17414 | 8/1994 |

OTHER PUBLICATIONS

"Sequencing of *Candida Albicans* at Stanford's DNA Sequencing and Technology Center" at <http://sequence-www.stanford.edu/group/candida/index.html> submitting 1 page (visited on Dec. 1, 2000).
Braun et al. (1997). "Control and filament formation in *Candida albicans* by the transcriptional repressor TUP1," *Science* 277:105–109.
*Animal Cell Culture: A practical approach,* R.I. Freshney, ed., (1987) IRL Press, Oxford (Table of Contents).
*Antibodies: A Laboratory Manual,* Ed Harlow et al., eds., (1988) Cold Spring Harbor Laboratory, New York (Table of Contents).
Bradway et al., "Do proline–rich proteins modulate a transglutaminase catalyzed mechanism of candidal adhesion?" (1993) *Crit. Rev. Oral Biol. Med.* 4: 293–299.
*Candida and candidosis,* F.C. Odds, ed., (1979) University Park Press (Table of Contents).

Cannon et al., "Oral Candida: Clearance, colonization, or candidiasis?" (1995) *J. Dental Research* 74:1152–1161.
*Cell Culture: Methods in Enzymology, vol. LVIII,* William B. Jakoby et al., eds., (1979) Academic Press (Table of Contents).
Church et al., "Genomic sequencing" (1984) *Proc. Natl. Acad. Sci. USA* 81:1991–1995.
*Contemporary Antifungal Therapy: Focus on Fluconazole. Pharmacotherapy* 10:133S–183S (1990) (Table of Contents).
*Current Protocols in Immunology, vol. I,* J.E. Coligan et al., eds., (1991) John Wiley & Sons, Inc., Supplement 28, (Table of Contents).
*Current Protocols in Molecular Biology,* F. M. Ausubel et al., eds., (1987) John Wiley & Sons, Inc., (Table of Contents).
de Bernardis et al., "Filamentous growth and elevated vaginopathic potential of a nongerminative variant of *Candida albicans* expressing low virulence in systemic infection" (1993) *Infect. Immun.* 61:1500–1508.
Dupont, Philip F., "*Candida albicans,* the opportunist. A cellular and molecular perspective"(1995) *J. Am. Podiatric Med. Assn.* 85:104–115.
Edmondson et al., "Repression domain of the yeast global repressor Tup1 interacts directly with histones H3 and H4" (1996) *Genes Dev.* 10:1247–1259.
Fidel, Jr. et al., "Candida–specific cell–mediated immunity is demonstrable in mice with experimental vaginal candidiasis" (1993) *Infect. Immun.* 61:1990–1995.
Fidel, Jr. et al., "A murine model of *Candida glabrata* vaginitis" (1996) *J. Infec. Disease* 173:425–431.
Fidel, Jr. et al., "Immunopathogenesis of recurrent vulvovaginal candidiasis" (1996) *Clin. Micro. Rev.* 9:335–348.
Fonzi et al., "Isogenic strain construction and gene mapping in *Candida albicans*" (1993) *Genetics* 134:717–728.
Fox et al., "Fluconazole resistant Candida in AIDS" (1991) *J. Infect. Dis.* 22:201–204.
*Gene Transfer Vectors for Mammalian Cells: Current Communications in Molecular Biology,* Jeffrey H. Miller et al., eds., (1987) Cold Spring Harbor Laboratory (Table of Contents).

(List continued on next page.)

*Primary Examiner*—Scott W. Houtteman
(74) *Attorney, Agent, or Firm*—Morrison & Foerster LLP

(57) ABSTRACT

The present invention provides RBT1 polynucleotides, including RBT1 polynucleotides encoding Rbt1, and Rbt1 polypeptides, from *Candida albicans.* Expression of the RBT1 gene is upregulated by the inactivation of the TUP1 gene and by environmental conditions that induce filamentous growth. Disruption of TUP1 finction in *C. albicans* is associated with filament fonnation as well as low infectivity. These RBT1 polynucleotide and Rbt1 polypeptide sequences (and anti-Rbt1 antibodies derived from Rbt1 polypeptides) may be used in methods of detecting *C. albicans* sequences in a biological sample. Further, the invention provides methods for screening agents which may control *C. albicans* virulence and compositions comprising these agents.

59 Claims, 3 Drawing Sheets

OTHER PUBLICATIONS

Gietz et al., "Studies on the transformation of intact yeast cells by the LiAc/SS–DNA/PEG procedure" (1995) *Yeast* 11:355–360.

Gillum et al., "Isolation of the *Candida albicans* gene for orotidine–5'–phosphate decarboxylase by complementation of *S. cerevisiae ura3* and *E. coli pyrF* mutations" (1984) *Mol. General Genetics* 198:179–181.

Gow et al., "A model for the germ tube formation and mycelial growth form of *Candida albicans*" (1984) *Sabouranudia* 22:137–143.

*Guide to Yeast Genetics and Molecular Biology: Methods in Enzymology* vol. 194 Christine Guthrie et al., eds., (1991) Academic Press (Table of Contents).

Hartley et al., "A deduced gene product from the Drosophila neurogenic locus, enhancer of split, shows homology to mammalian G–protein β subunit" (1988) *Cell* 55:785–795.

Herlyn et al., "Anti–idiotypic antibodies bear the internal image of a human tumor antigen" (1986) *Science* 232:100–102.

Hill et al., "DMSO enhanced whole cell yeast transformation" (1991) *Nucleic Acids Res.* 19:5791.

Horn et al.. "Cancer gene therapy using plasmid DNA: Purification of DNA for human clinical trials" (1995) *Human Gene Therapy* 6:565–573.

Hubank et al., "Identifying differences in mRNA expression by representational difference analysis of cDNA" (1994) *Nucleic Acids Res.* 22:5640–5648.

*Immunochemistry and Molecular Immunology. Weir's Handbook of Experimental Immunology,* Fifth Edition, vol. I, , D.M. Weir et al., eds., (1996) Blackwell Science, Cambridge, MA, (Table of Contents).

Keleher et al., "Ssn6–Tup1 is a general repressor of transcription in yeast" (1992) *Cell* 68:709–719.

Kerridge, David, "Fungal dimorphism: A sideways look" (1993) *Dimorphic Fungi in Biology and Medicine* Bossche et al., eds., Plenum Press, NY, pp. 3–10.

Komachi et al., "The WD repeats of Tup1 interact with the homeo domain protein α2" (1994) *Genes Dev.* 8:2857–2867.

Komachi et al., Residues in the WD repeats of Tup1 required for interaction with α2 (1997) *Mol. Cell. Biol.* 17:6023–6028.

Lambrechts et al., "Muc1, a mucin–like protein that is regulated by Mss10, is critical for pseudohyphal differentiation in yeast" (1996) *Proc. Natl. Acad. Sci. USA* 93:8419–8424.

Lee et al., "An amino acid liquid synthetic medium for the development of mycelial and yeast forms of *Candida albicans*" (1975) *Sabouraudia* 13:148–153.

Lemontt et al., "Pleiotropic mutations at the tupi locus that affect the expression of mating–type–dependent functions in *saccharomyces cerevisiae*" (1980) *Genetics* 94:899–920.

Lisitsyn et al., "Representational difference analysis in detection of genetic lesions in cancer" (1995) *Meth. Enz.* 254:291–304.

Lisitsyn et. al., "Cloning the differences between two complex genomes" (1993) *Science* 259: 946–951.

Llevadot et al.. "Genomic organization of TUPLE1/HIRA: a gene implicated in DiGeorge syndrome" (1996) *Mammalian Genome* 7:911–914.

Lo et al., "FLO11, a yeast gene related to the STA genes, encodes a novel cell surface flocculin" (1996) *J. Bacteriol.* 178:7144–7151.

Lo et al., "Nonfilamentous *C. albicans* mutants are avirulent" (1997) *Cell* 90: 939–949.

Marquis et al., "Strain–dependent differences in susceptibility in mice to experimental candidosis" (1986) *J. Infect. Dis.* 154:906–909.

Merrifield, R.B., "Solid phase peptide synthesis. I. The synthesis of a tetrapeptide" (1963) *J. Am. Chem. Soc.* 85:2149–2154.

*Molecular Cloning: A Laboratory Manual,* Second Edition, J. Sambrook et al., eds., (1989) Cold Spring Harbor Laboratory Press, (Table of Contents).

Odds, Frank C., "Morphogenesis in *Candida albicans*" (1985) *Crit. Rev Microbiol.* 12:45–93.

Odds, Frank C., "Candida infections: An overview." (1987) *Crit. Rev. Microbiol.* 15:1–5.

Odds, Frank C., "Candida species and virulence" (1994) *ASM News* 60:313–318.

Odds, Frank C., "Pathogenesis of Candida infections" (1994) J. Am. Acad. Dermatol.31:S2–S5.

Oi et al., "Chimeric antibodies" (1986) *BioTechniques* 4:214–221.

*Oligonucleotide Synthesis: A Practical Approach,* M.J. Gait, ed., (1984) IRL Press, Oxford, (Table of Contents).

Paya, Carlos V., "Fungal infections in solid–organ transplantation" (1993) *Clin. Infect. Dis.* 16:677–688.

Posnett et al., "A novel method for producing anti–peptide antibodies" (1988) *J. Biol. Chem.* 263:1719–1725.

Redd et al., "A complex composed of Tup1 and Ssn6 represses transcription in vitro" (1997) *J. Biol. Chem.* 272: 11193–11197.

*Remington's Pharmaceutical Sciences, 18th Edition,* A.R. Gennaro, ed., (1990) Mack Publishing Co., Easton, PA, (Table of Contents).

Rubin, R.H., "Fungal and bacterial infections in the immunocompromised host" (1993) *Eur. J. Clin. Micro. Infect. Dis.* 12 (Suppl. 1):S42–S48.

San–Blas et al., "Molecular aspects of fungal dimorphism" (1984) *Crit. Rev. Microbiol.* 11:101–127.

Scherer et al., "Genetics of *Candida albicans*" (1990) *Microbiological Rev.* 54:226–241.

Shepherd, Maxwell G., "Pathogenicity of morphological and auxotrophic mutants of *Candida albicans* in experimental infections" (1985) *Infect. Immunity* 50:541–544.

Simon et al., "Diversity of G proteins in signal transduction" (1991) *Science* 252:802–808.

Spira et al., "The identification of monoclonal class switch variants by sib selection and an ELISA assay" (1984) *J. Immunol. Meth.* 74:307–315.

Stabb et. al., "Developmental expression of a tandemly repeated, proline– and glutamine–rich amino acid motif on hyphal surfaces of *candida albicans*" (1996) *J. Biol. Chem.* 271:6298–6305.

Steplewski et al., "Isolation and characterization of anti–monosialoganglioside monoclonal antibody 19–9 class–switch variants" (1985) *Proc. Natl. Acad. Sci. USA* 82:8653–8657.

Stitt et al., "The anticoagulation factor protein S and its relative, Gas6, are ligands for the Tyro 3/Axl family of receptor tyrosine kinases" (1995) *Cell* 80:661–670.

Tam, James P., "High–density multiple antigen–peptide system for preparation of antipeptide antibodies" (1989) *Meth. Enzymol.* 168:7–15.

*The Polymerase Chain Reaction,* K.B. Mullis et al., eds., (1994) Birkhäuser, Boston, MA, (Table of Contents).

Tzamarias et al., "Functional dissection of the yeast Cyc8–Tup1 transcriptional co–repressor complex" (1994) *Nature* 369:758–761.

*Vectors,* Peter Gacesa et al., eds., (1994) John Wiley & Sons, (Table of Contents).

Wahi et al., "Identification of genes required for α2 repression in *Saccharomyces cerevisiae*" (1995) *Genetics* 140:79–90.

Wall et al., "The structure of the G protein heterotrimer $G_{i\alpha 1}\beta_1\gamma 2$" (1995) *Cell* 83:1047–1058.

Warren et al., "Yeasts of medical importance" *Manual of Clinical Microbiology* (1991) 5th ed., Chapter 60, pp. 617–629.

Weinberg et al., "Severe combined immunodeficiency due to a specific defect in the production of interleukin–2" *N. Eng. J. Med.* (1990) 332:1718–1723, 1741–1743.

Williams et al., "Characterization of TUP1, a mediator of glucose repression in *saccharomyces cerevisiae*" (1990) *J. Mol. Cell. Biol.* 10:6500–6511.

Williamson, Michael P., "The structure and function of proline–rich regions in proteins" (1994) *Biochem J.* 297:249–260.

Yochem et al., "Structural comparison of the yeast cell division cycle gene CDC4 and a related pseudogene" (1987) *J. Mol. Biol.* 195:233–245.

Fig. 2A

RBT1 cDNA clone

```
tgccccagaatcatctgctccagaatctagtgccccagaatcatctgcaccagtcactgaaacaccaactg
gtccagtttccactgttactgagcaatcaaagaccatcgtcaccatcacctcatgctccaacaatgcatgc
agtgaatctaaggtcaccactggtgttgttgttgttacatctgaagatactgtttacactacattctgtcc
attaactgaaactactccagctactgaatcagccccagaatcatctgcaccagccactgaatcagttccag
ctactgaaagtgctccagttgctccagaatcatctgcacca
```

Fig. 2B

Translation of RBT1 polypeptide from cDNA clone

| | | | | | | | | | | | | | | |
|---|---|---|---|---|---|---|---|---|---|---|---|---|---|---|
| Ala | Pro | Glu | Ser | Ser | Ala | Pro | Glu | Ser | Ser | Ala | Pro | Glu | Ser | Ser | Ala |
| 1 | | | | 5 | | | | | 10 | | | | | 15 | |
| Pro | Val | Thr | Glu | Thr | Pro | Thr | Gly | Pro | Val | Ser | Thr | Val | Thr | Glu | Gln |
| | | | 20 | | | | | 25 | | | | | 30 | | |
| Ser | Lys | Thr | Ile | Val | Thr | Ile | Thr | Ser | Cys | Ser | Asn | Asn | Ala | Cys | Ser |
| | | 35 | | | | | 40 | | | | | 45 | | | |
| Glu | Ser | Lys | Val | Thr | Thr | Gly | Val | Val | Val | Val | Thr | Ser | Glu | Asp | Thr |
| | 50 | | | | | 55 | | | | | 60 | | | | |
| Val | Tyr | Thr | Thr | Phe | Cys | Pro | Leu | Thr | Glu | Thr | Thr | Pro | Ala | Thr | Glu |
| 65 | | | | | 70 | | | | | 75 | | | | | 80 |
| Ser | Ala | Pro | Glu | Ser | Ser | Ala | Pro | Ala | Thr | Glu | Ser | Val | Pro | Ala | Thr |
| | | | | 85 | | | | | 90 | | | | | 95 | |
| Glu | Ser | Ala | Pro | Val | Ala | Pro | Glu | Ser | Ser | Ala | Pro | | | | |
| | | | 100 | | | | | 105 | | | | | | | |

Fig. 3A

RBT1 genomic clone

```
tatctttgtcattataaggcgtgttttggttttggttttggggttttgttttttcgttttaatgcaagaa
tcttagctttgttttgcatgattttcgggtttaatgcatagtgcgatatttgataaccctggcacagcatc
tttgtttccactaatgttcattgcatttttaaaattttcagtacccyacgccaattaaaccaaatacccy
ccaatgctttgtctcgcaataattaaacattttcaagaatgttctcttttttagattttycaattctttgt
tttttaatcacaaatatgaaaacattttcgacagattcgttttagtattttttataattctacacaaagtta
aattttcacactgttttaagttcgacttyggaatgttaatgcttyctatttttcaattcggatcttgaaa
gacaattacccgttgatttcaacaattaatcaatggttataatatgatcaaattactttcccaaaaactat
aaataaaggtaagatttaccggatttygaacttgtaattttcttattttctatcccatcaacaagatcaa
acaaaatacaaatctcgtattattcattcgctttaattttyatcaactATGAGATTTGCAACTGCCCAACT
CGCTGCCCTCGCTTACTACATTTTATCCACTGAGGCTACTTTCCCATTATTGGGTGACATCTTTAATTGTA
TTCCACACAACACTCCTCCTGTCTGTACTGACTTGGGTCTTTACCACGATAGCTCCATTTCCCTTAGTGGT
TCCAAGAACAAGAGAGAAGCTGAAATTGTCAATGAAGATGGTACAATTGAAAAGAGAACTTTTGGAAGCGC
TGGTGTAAATGCCGGTTTCAATGCCGCATTTGTCGTGTCTAATGCCAAAAAATTATCTGACGGTTCTTATG
GTATTGATTGTAACTTCAAGAGTGATTCTTCTGTCCAATTGAACCTGGCCTTTGGTAAAAAAGTTAAACAA
TTGAGTATCACCGGTACTGGTTATTCTGATATTTCATTATTAGGAAATGTTGCTAATCCATTTGAATGGTC
AGCTTCCTTGAAAGTCAAAGCAGAAATTGTTAAAGGAAAATGTTGTCTTCCATCAGGTTTCAGAATCGTTA
CAGATTTCGAAAGCAACTGTCCTGAATTTGATGCCATCAAACAATTTTTTGGCAGTTCTCAAATAATTTAC
AAAGTCAATGCCGTTTCTAACGCAATTGGTACTTTTGATGCTTCTGCATTATTCAATGCTCAAGTCAAAGC
CTTCCCTGCCAAGAGAGAATTAGATGAATTTGAAGAATTAAGTAACGATGGTGTTACTCACAGCAAGAGAA
CTTTGGGTTTGCTTTTGGGTTTGCTTAAGAAAGTTACTGGTGGATGTGATACTTTACAACAATTCTGTTGG
GACTGTCAATGTGACACCCCATCTCCATCAACTACCACCGTAAGTACTTCATCTGCTCCATCTACTTCCCC
AGAATCATCTGCTCCATCTACTACTACAGTTACCACTTCATCTTCTCCAGTTACTTCTCCAGAATCTAGTG
TTCCAGAAACTACTACCGTTACTACTTCATCTGTCCCAGAAACTACTCCAGAATCATCAGCTCCAGAAACC
ACCACAGTTACTACTTCATCTGTTCCTTCTACTACCCCAGAGTCTTCTGCTCCAGAAACCACTCCAGAATC
ATCAGCTCCAGAATCTAGTGTTCCAGAATCATCAGCTCCAGAAACCACTCCAGAATCATCAGCTCCAGAAT
CTAGTGTTCCAGAATCATCAGCTCCAGAAACTGAAACTGAAACCACTCCAACTGCTCACTTAACTACTACT
ACTGCTCAAACTACTACTGTTATAACTGTTACTTCATGCTCTAACAATGCTTGTAGCAAAACTGAAGTAAC
CACAGGTGTTGTTGTTGTCACTTCTGAAGATACTATTTACACTACCTTCTGTCCATTAACTGAAACCACCC
CAGTTCCTTCAAGTGTTGATTCTACTTCAGTCACTTCTGCTCCAGAAACCACCCCAGAATCTACTGCCCCA
GAATCATCTGCTCCAGAATCTAGTGCCCCAGAATCATCTGCACCAGTCACTGAAACACCAACTGGTCCAGT
TTCCACTGTTACTGAGCAATCAAAGACCATCGTCACCATCACCTCATGCTCCAACAATGCATGCAGTGAAT
CTAAGGTCACCACTGGTGTTGTTGTTGTTACATCTGAAGATACTGTTTACACTACATTCTGTCCATTAACT
GAAACTACTCCAGCTACTGAATCAGCCCCAGAATCATCTGCACCAGCCACTGAATCAGTTCCAGCTACTGA
AAGTGCTCCAGTTGCTCCAGAATCATCTGCACCAGGTACTGAAACCGCACCAGCTACCGAATCAGCTCCTG
CCACTGAAAGTTCTCCAGTTGCTCCAGGTACTGAATCTTCCCCAGTTGCCCCAGAATCATCAGCACCAGCT
ACTGAATCAGCACCAGCCACCGAATCTTCCCCAGTTGCTCCAGGTACTGAAACCACTCCAGCTACTCCAGG
TGCTGAATCAACTCCAGTTGCTCCAGTTGCCCCAGAATCATCAGCTCCAGCTGTTGAATCTTCTCCAGTTG
CTCCAGGTGTCGAAACTACTCCAGTTGCACCAGTTGCTCCTTCTACCACTGCAAAAACTAGTGCTCTCGTC
TCTACGACTGAGGGTACTATTCCAACTACATTAGAATCTGTTCCTGCCATTCAACCATCTGCTAACTCCTC
ATACACTATTGCTTCAGTCTCTTCATTCGAAGGTGCTGGTAACAACATGAGATTAACTTATGTGCTGCTA
TTATTGGTCTTGCTGCATTCTTGATCtaattctagttactgatactatatcttttttcttttttctgtttgga
tttctactaattacatttttcaattttcggttttcaatattatgacaaaggttattgtattgaatatttac
tttggtacataaaaaaagttggtgcttttttttcttttagaattgttttgtttagatttcgtattttcttc
ttattctgcttttcatttycggtgtatagattacaacttacaataaataccatttttttctattaaattt
ttcatcacattgattagttttcaacttgaaaagaattcgaattg
```

Fig. 3B

Translation of open reading frame in RBT1 genomic clone

```
MRFATAQLAALAYYILSTEATFPLLGDIFNCIPHNTPPVCTDLGLYHDSSISLSGSKNKREAEIVNEDGTI
EKRTFGSAGVNAGFNAAFVVSNAKKLSDGSYGIDCNFKSDSSVQLNLAFGKKVKQLSITGTGYSDISLLGN
VANPFEWSASLKVKAEIVKGKCCLPSGFRIVTDFESNCPEFDAIKQFFGSSQIIYKVNAVSNAIGTFDASA
LFNAQVKAFPAKRELDEFEELSNDGVTHSKRTLGLLLGLLKKVTGGCDTLQQFCWDCQCDTPSPSTTTVST
SSAPSTSPESSAPSTTVTTSSSPVTSPESSVPETTTVTTSSVPETTPESSAPETTTVTTSSVPSTTPESS
APETTPESSAPESSVPESSAPETTPESSAPESSVPESSAPETETETTPTAHLTTTTAQTTTVITVTSCSNN
ACSKTEVTTGVVVVTSEDTIYTTFCPLTETTPVPSSVDSTSVTSAPETTPESTAPESSAPESSAPESSAPV
TETPTGPVSTVTEQSKTIVTITSCSNNACSESKVTTGVVVVTSEDTVYTTFCPLTETTPATESAPESSAPA
TESVPATESAPVAPESSAPGTETAPATESAPATESSPVAPGTESSPVAPESSAPATESAPATESSPVAPGT
ETTPATPGAESTPVAPVAPESSAPAVESSPVAPGVETTPVAPVAPSTTAKTSALVSTTEGTIPTTLESVPA
IQPSANSSYTIASVSSFEGAGNNMRLTYGAAIIGLAAFLI
```

POLYNUCLEOTIDE SEQUENCES FROM *CANDIDA ALBICANS* ENCODING POLYPEPTIDES ASSOCIATED WITH FILAMENTOUS GROWTH

CROSS-REFERENCE TO RELATED APPLICATIONS

The present application claims the priority benefit of U.S. Provisional Patent Application No. 60/068,065, filed Dec. 18, 1997 and of U.S. Provisional Patent Application No. 60/061,058, filed Oct. 2, 1997.

STATEMENT OF RIGHTS TO INVENTIONS MADE UNDER FEDERALLY SPONSORED RESEARCH

This invention was made in part during work supported by a grant from the National Institutes of Health (NIH) RO1 GM 37049. The government has certain rights in this invention.

TECHNICAL FIELD

This invention relates to polynucleotides and protein products encoded thereby. More specifically, the invention relates to polynucleotides of *C. albicans* and polypeptides encoded by the polynucleotides, which are associated with TUP1 gene fimction, particularly, gene repression and morphological transition, particularly to a filamentous form.

BACKGROUND OF INVENTION

The yeast Candida is a ubiquitous human commensal, known as the causative agent of candidiasis. The majority of the diseases are caused by the species *Candida albicans*. It is the most prevalent commensal and opportunistic fungal pathogen of humans, causing common superficial infections as well as more serious systemic and organ infections. Cannon et al. (1995) *J. Dental Research* 74:1152–1161. Exposure to *C. albicans* at or shortly after birth results in lifelong colonization in the host tissues, such as the gastrointestinal tract, oral cavity and genital area. It has been noted that approximately 75% of women would suffer from vaginal candidiasis at some stage in their lifetime. Bossche et al. (1993) *Fungal Dimorphism* 3–10; Fidel et al. (1996) *Clin. Micro. Rev.* 9(3):335–348. Whereas *C. albicans* infection often remains localized to the initial sites of contact in healthy individuals, *C. albicans* cells can invade submucosal vessels, disseminate hematogenously and become life-threatening, especially to immunocompromised patients. The invasive forms of *C. albicans* infection are not only dangerous in their own right, but they are believed to facilitate infections by other opportunistic pathogens.

In the last decades, the incidence of severe and systemic candidiasis has increased dramatically because of the growing number of immunocompromised patients suffering from AIDS, diabetes, cancer and other conditions. In addition, the widespread use of immunosuppressants for organ transplant patients, the common practice of radiation and chemotherapy for treating malignancies, as well as the growing size of the aging population have increased the morbidity of this opportunistic pathogen. For reviews, see Rubin et al. (1993) *Eur. J. Clin. Microbiol. Infect. Dis.* 12 Suppl. 1, 542; Dudley et al. (1990) *Pharmacotherapy 10:133*; Paya (1993) *Clin. Infect. Dis.* 16:677–688; Rubin (1993) *Eur. J. Clin. Micro. Infect. Dis.* 12 Suppl. 1:S42–S48.

Despite decades of intensive study, the properties of *C. albicans* that contribute to its virulence are only beginning to be understood. Among the most investigated virulence factors are adherence, production of hydrolytic enzymes and adoption of various cell morphologies. Odds et al. (1994) *Am. Soc. Microbiol. News* 60:313–318. The ability of *C. albicans* to adhere to the host surfaces probably allows initial colonization and infection of the host tissues. Secretion of a variety of hydrolytic enzymes which are capable of degrading proteins and lipids is thought to generate tissue cavitation and thereby facilitate deeper penetration. The morphological transition between various forms of *C. albicans* is also considered a key determinant of virulence.

*C. albicans* cells can exist in a variety of shapes, ranging from ellipsoidal budding yeast cells (also known as blastospores) to filamentous forms in which cells remain attached to each other after dividing and thereby form long branched strings of connected cells. These filamentous forms include both pseudohyphae (where cells that form filaments are elongated, but still ellipsoidal) and true hyphae (where highly elongated cells that form the filaments are cylindrical and are separated by perpendicular septal walls). Transitions between the ellipsoidal and filamentous forms take place by outgrowth of new cells with the altered morphology, rather than remodeling of pre-existing cells. The ability of *C. albicans* to adopt these different morphologies is thought to allow the fungus to adapt to, and possibly travel to, different host micro-environments. Odds et al. (1988) *Candida and Candidosis* (Bailliere Tindall, London, 2nd ed.); Odds et al. (1994); Odds et al. (1994) *J. Am. Acad. Dermatol.* 31:52. The regulation of cellular morphology is in response to environmental conditions. In vitro studies have shown that most *C. albicans* strains assume filamentous forms when they are subjected to either unfavorable growth conditions, such as nutrient-poor media and high $CO_2:O_2$ ratio, or host-mimicking conditions, such as high temperature (37° C.) and mammalian serum (10%). Conversely, rich media, low temperatures and aerated conditions promote blastospore growth. Intermediate conditions can induce various pseudohyphal forms as well as true hyphae. For reviews, see Odds et al. (1988) *Candida and Candidosis*, Bailliere Tindall, London, ed. 2nd; Odds et al *Crit. Rev Microbiol.* (1985) 12:45; Gow et al. (1984) *Sabouraudia* 22:137. Very little is known about the genetic identity of regulators controlling the morphological transition of *C. albicans*.

The ability of *C. albicans* to adopt these different morphologies is thought to contribute to colonization and dissemination within host tissues and thereby to promote infection. Odds (1988); Odds (1994) *J. Am. Acad. Dermatol.* 31:S2. It has been commonly suggested that the hyphal form is invasive and pathogenic, while the blastospore is the commensal, non-pathogenic form. However, all morphological forms have been found within infected tissues. Histopathological examination of candidiasis lesions indicates that hyphae are not always present. More recent studies have shown that commensal *C. albicans* does not exist uniquely in the blastospore form. In fact, sometimes invading *C. albicans* cells are seen exclusively as the budding yeast form. Odds et al. (1994) *Am. Soc. Microbiol. News* 60:313–318. Despite the uncertainty with regard to the relative roles these two distinct forms of *C. albicans* have in fungal virulence, phenotypic switching represents a remarkable adaptation that *C. albicans* has acquired to cope with different host microenvironments.

The TUP1 gene of *C. albicans* appears to be a key regulator of filamentous growth. Braun et al. (1997) *Science* 277:105–109. Cells in which TUP1 function is disrupted grow exclusively as filaments in all conditions tested (e.g., nutrient-rich and nutrient-poor media, in the presence and absence of mammalian serum, aerobic and micro-aerobic conditions, throughout the range of temperature and pH values). These results suggest that the gene product Tup1 is a repressor of filamentous development. This function for the Tup1 protein may occur through transcriptional repression of genes whose expression is required to initiate and/or maintain filamentous growth. This conclusion is supported by: (1) the amino acid sequence of C. albicans Tup1 protein is very similar (67% identity) to that of the S. cerevisiae Tup1 protein, a known transcriptional repressor, and (2) expression of the C. albicans TUP1 gene is S. cerevisiae lacking TUP1 function restored wild type cell shape and growth behavior to the S. cerevisiae cells indicating that C. albicans TUP1 gene product functionally complements (i.e., substitutes for) S. cerevisiae tup1 (i.e., lacking Tup1 fimction). For papers describing S. cerevisiae TUP1, see Tzamarias et al. (1994) Nature 369: 758; Komachi et al. Genes Dev. 8: 2857; Wahi et al. (1995) Genetics 140: 79–90; Edmondson et al. (1996) Genes Dev. 10: 1247.

Current therapy available for systemic candidiasis is limited to the use of anti-fungal agents. In practice, the arsenal of anti-fingal drugs is based on a few antimycotics, such as flucytosine, amphotericin B and azole derivatives. Many of these antimycotics are somewhat water insoluble which restrict their bioavailability and present problems in intravenous formulation. In addition, they cause serious and often difficult side effects, such as renal toxicity, bone marrow destruction, as well as unpleasant symptoms such as fever and shivering. Furthermore, the chronic use of these anti-fungal agents has led to the emergence of drug-resistant strains of Candida, which can cause fatal relapse of the disease. Dupont et al. (1995) *J. Am. Podiatric Med. Assn.* 85:104–115; Fox et al. (1991) *J. Infect. Dis.* 22:201–204; Scheife (1990) *Pharmacotherapy* 10:S133–S183. Taken together, anti-fungal therapy alone is inadequate for treating chronic candidiasis. The availability of recombinant cytokines, such as interleukin-2, provides an alternative way to stimulate the cell-mediated immunity of infected individuals. However, this type of cytokine replacement therapy for fungal infections remains highly experimental. Weinberg et al. (1990) *N. Eng. J. Med.* 332: 1718.

The transition between blastospore and filamentous forms may play a significant role in the pathogenicity of this organism. Mutant strains of C. albicans which failed to form filaments were found to be avirulent in a mouse infection model. Lo et al. (1997) *Cell* 90: 939–949. However, the C. albicans tup1 knockout mutant, which grows exclusively in filaments, is also poorly infective in mice. Braun et al. (1997); U.S. Ser. No. 60/051552. Identifying the genes regulated by TUP1, and thus that contribute to this morphological transition to growth in filaments and decreased infectivity, are therefore of great significance for identifying the role of this transition in pathogenesis and for developing potential therapeutic agents of candidiasis.

In view of the alarming prevalence of life-threatening candidiasis among immunocompromised patients and the lack of satisfactory agents to treat this condition, there is a pressing need for developing better therapeutic agents to combat C. albicans infections.

All publications cited herein are hereby incorporated by reference in their entirety.

SUMMARY OF THE INVENTION

This invention provides C. albicans RBT1 gene polynucleotide sequences, Rbt1 polypeptides encoded by these sequences, antibodies that bind to these polypeptides, compositions comprising any of the above, as well as methods using the polynucleotides, polypeptides, and/or antibodies.

Accordingly, in one aspect, the invention includes an isolated polynucleotide comprising a sequence encoding an Rbt1 polypeptide from C. albicans. The Rbt1 polypeptide encoded is found within the sequence depicted in SEQ ID NO:4 and embodiments included, including from about amino acid 1 to amino acid about 23, about amino acid 480 to about amino acid 496 of SEQ ID NO:4, as well as the sequence of SEQ ID NO:2, as well as the sequence of SEQ ID NO:4.

In another aspect, the invention provides isolated polynucleotides based on the sequence depicted in SEQ ID NO:3, and as such may comprise nucleotides from about 617 to about 685, from about 2054 to about 2104, from about 617 to about 2866 of SEQ ID NO:3, as well as the sequence of SEQ ID NO:1, as well as the sequence of SEQ ID NO:3.

In another aspect, the invention provides an isolated polynucleotide comprising the polynucleotide sequence of SEQ ID NO:3. In another aspect, the isolated polynucleotide comprises a region of at least 20 contiguous nucleotides, with the region having at least 75%, preferably 85%, sequence identity with a sequence depicted in SEQ ID NO:3.

In another aspect, the invention provides an isolated polynucleotide comprising the polynucleotide sequence of SEQ ID NO: 1. In another aspect, the isolated polynucleotide comprises a region of at least 20 contiguous nucleotides, with the region having at least 75%, preferably 85%, sequence identity with a sequence depicted in SEQ ID NO:1.

In another aspect, the invention includes cloning vectors, expression vectors, host cells, and compositions comprising any of the above polynucleotides.

In another aspect, the invention provides an isolated polypeptide comprising an Rbt1 polypeptide sequence from C. albicans. The Rbt1 polypeptide(s) is found within the sequences depicted in SEQ ID NO:2 and SEQ ID NO:4, including from about amino acid 1 to about amino acid 23, about amino acid 480 to about amino acid 496 of SEQ ID NO:4, as well as the sequence of SEQ ID NO:2, as well as the sequence of SEQ ID NO:4.

In another aspect, the isolated polypeptide comprises a region of at least 10 contiguous amino acids which have at least 70% sequence identity to a sequence depicted in SEQ ID NO:4 wherein expression of said at least 10 amino acids is increased during conversion of C. albicans to filamentous form.

In another aspect, the isolated polypeptide comprises a region of at least 10 contiguous amino acids which have at least 70% sequence identity to a sequence depicted in SEQ ID NO:2 wherein expression of said at least 10 amino acids is increased during conversion of C. albicans to filamentous form.

In another aspect, the invention includes compositions comprising any of the polypeptides of the invention.

In another aspect, the invention provides purified antibodies that are capable of specifically binding to a polypeptide of the invention. in another aspect, the invention provides a monoclonal antibody capable of specifically binding to a polypeptide of the invention.

In another aspect, the invention provides a method for detecting a polynucleotide from C. albicans in a sample comprising the steps of (a) contacting polynucleotide from C. albicans from a sample with a polynucleotide of this invention under conditions that permit the formation of a stable duplex; and (b) detecting the stable duplex formed in step (a), if any.

The invention also provides a method for detecting a polynucleotide from C. albicans in a sample comprising the steps of (a) conducting an amplification reaction on a polynucleotide in the sample using a primer consisting of a fragment of the polynucleotide sequence of SEQ ID NO:1 or SEQ ID NO:3; and (b) detecting the presence of amplified copies of the polynucleotide, if any.

The invention also provides a method for detecting an anti-C. albicans Rbt1 antibody in a biological sample, comprising the steps of: (a) contacting antibody from the sample with a polypeptide of this invention under conditions which permit formation of a stable antigen-antibody complex; and (b) detecting said stable complexes formed in step (a), if any.

The invention also provides a method for detecting a C. albicans Rbt1 polypeptide in a biological sample, comprising the steps of: (a) contacting polypeptide from the biological sample with an antibody of this invention under conditions that permit the formation of a stable antigen-antibody complex; and (b) detecting said stable complexes formed in step (a), if any.

In another aspect, the invention provides methods for identifying an agent that may control virulence in C. albicans. These methods may be in vitro or in vivo (i.e., cell-based). In one embodiment, the invention provides a method for identifying an agent that may control virulence in C. albicans, said method comprising:

(a) contacting at least one agent to be tested with a suitable host cell that has RBT1 function;

(b) analyzing at least one characteristic which is associated with a modulation of RBT1 function in said host cell, wherein an agent is identified by its ability to elicit at least one such characteristic.

In another aspect, the invention provides compositions for controlling virulence in C. albicans comprising any agent identified by the screening methods above.

In another aspect, the invention provides kits for detection or quantification of (a) a polynucleotide comprising an RBT1 polynucleotide from C. albicans; or (b) a C. albicans Rbt1 polypeptide; or (c) an anti-C. albicans Rbt1 antibody in a biological sample. These kits contain (a) a polynucleotide of the invention; or (b) an antibody of the invention; or (c) a polypeptide of the invention, respectively.

In another aspect, the invention provides methods of isolating a polynucleotide sequence from C. albicans that is associated with C. albicans RBT1 function, comprising identifying a transcribed polynucleotide which is up-regulated upon RBT1 expression.

In another aspect, the invention provides methods of inhibiting virulence of C. albicans comprising modulating C. albicans RBT1 function.

Figure 1:
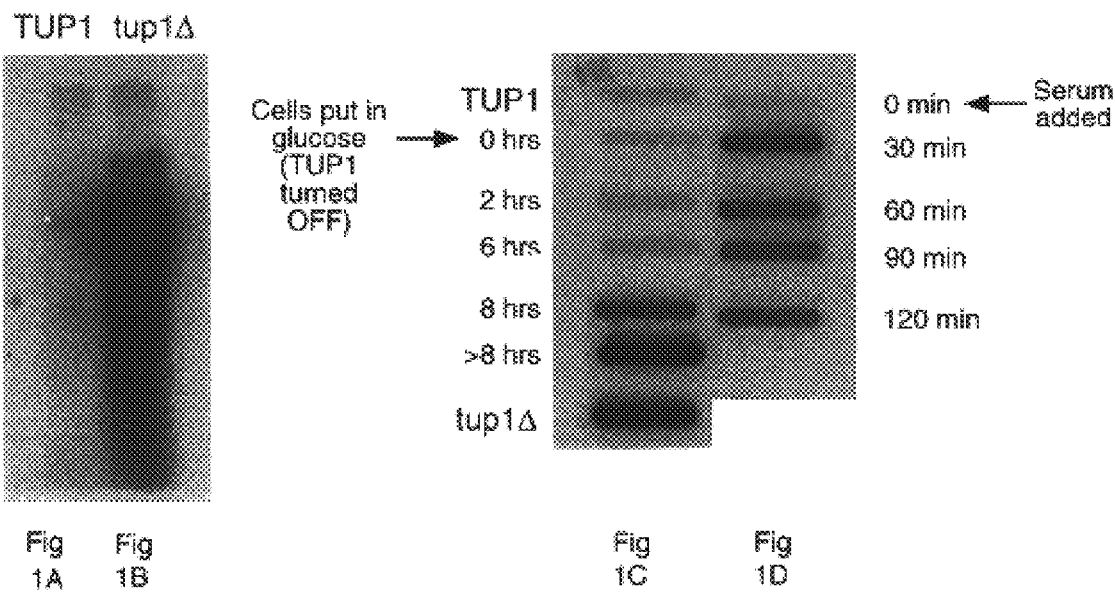
FIGS. 1(A)–(D) are halftone reproductions of autoradiograpbs depicting the expression of RBT1 MRNA from C. albicans cells: (A) wild type (TUP1), (B) tup1 mutant (tup1Δ), (C) a modified strain of C. albicans in which TUP1 expression is repressed when glucose is the sole carbon source, (D) wild type cells grown in serun.

The expression of RBT1 mRNA is greatly up-regulated in cells lacking TUP1 function and in wild type cells grown in serum.

FIGS. 2(A)–(B) provide the polynucleotide (A; SEQ ID NO:1) and amino acid (B; SEQ ID NO:2) sequences of a fragment of RBT1 cDNA.

FIGS. 3(A)–(B) provide the polynucleotide sequence of C. albicans genomic DNA of which contains the RBT1 gene (A; SEQ ID NO:3) and Rbt1 amino acid sequence encoded within the open reading frame of the genomic DNA (B; SEQ ID NO:4). The nucleotides of the open reading frame are illustrated in capital letters of FIG. 3(B).

MODES FOR CARRYING OUT THE INVENTION

We have discovered a C. albicans polynucleotide sequence and the polypeptide encoded thereby, both of which are associated with C. albicans TUP1 gene function, more particularly, morphological transition. The TUP1 gene appears to be an important regulator of the cell morphology of C. albicans. Braun et al. (1997). By experimentally verified analogy to the TUP1 gene of S. cerevisiae, a general transcriptional repressor, C. albicans Tup1 may accomplish this control through the repression of genes necessary for filamentous growth. The loss of TUP1 function in C. albicans results in a shift from growth as single, ellipsoidal cells to growth exclusively in filaments. The conversion between the filamentous and non-filamentous morphological state is believed to play an important role in C. albicans pathogenesis and virulence. Loss of TUP1 function, and the resulting filamentous growth, is associated with dramatically lower infectivity of C. albicans in a mouse model (see U.S. Ser. No. 60/051552).

Briefly, the polynucleotide sequence (and polypeptide sequence encoded thereby) was obtained by (a) identifying mRNA sequences that were de-repressed (induced) upon loss of TUP1 function and (b) determining which of the sequences from (a) were expressed during serum stimulation of filamentous growth.

Because of the fimctional basis for obtaining the polynucleotide (and polypeptide encoded by this polynucleotide) described herein, the polynucleotide and polypeptide sequences of this invention have a variety of uses, including, but not limited to, diagnostics, screening methods, and indicators of TUP1 function.

Bacteria containing the cloned RBT1 genomic DNA has been deposited with the American Type Culture Collection (ATCC), 12310 Parklawn Drive, Rockville, Md., U.S.A. 20852 on Nov. 21, 1997, under the provisions of the Budapest Treaty for the International Recognition of the Deposit of Microorganisms for the Purposes of Patent Procedure. The bacterial culture, DH5α::p499(3-1), was accorded the ATCC designation number 98595.

A more detailed description of these sequences, as well as how these sequences were obtained, is provided below.

Definitions

As used herein, "RBT1" or "RBT1 gene" refers to the C. albicans RBT1 gene. Unless otherwise specified, the terms "RBT1" and "C. albicans RBT1" are interchangeable. The sequence of RBT1 is depicted within SEQ ID NO:3 (see also FIG. 3). A "fragment" or "region" of RBT1 is a portion of the RBT1 gene, and as such may contain coding and/or non-coding sequences. For example, SEQ ID NO: 1 contains a fragment of the RBT1 coding sequence (see also FIG. 2). Preferably, a fragment of RBT1 comprises at least 10 contiguous nucleotides, more preferably at least 15, more preferably at least 25, more preferably at least 30, more preferably at least 50, more preferably at least 100, more preferably at least 150, more preferably at least 200, more preferably at least 250, more preferably at least 300 contiguous nucleotides.

"Rbt1" refers to a protein (polypeptide) product encoded in the C. albicans RBT1 gene. Unless otherwise specified, the terms "Rbt1" and "C. albicans Rbt1" are interchangeable. SEQ ID NO:4 depicts a conceptual translation of an open reading frame of RBT1. A "fragment" or "region" of Rbt1 (i.e., full-length) is a portion of the RBT1 gene product. SEQ ID NO:2 depicts a fragment of Rbt1. It is understood that Rbt1 may exist in more than one form, such as a single Rbt1 polypeptide, an assembly of at least one Rbt1 polypeptide, and/or within a complex (i.e., comprising multi-subunits) containing at least one Rbt1 polypeptide with at least one other polypeptide. Rbt1 may also exist in more than one form due to alternative splicing.

An "RBT1 polynucleotide" refers to any of the polynucleotide embodiments described herein. An "Rbt1 polypeptide" refers to a polypeptide product encoded by or within RBT1 (i.e., full-length and/or a fragment of RBT1); thus, a "Rbt1 polypeptide" refers to any of the polypeptide embodiments described herein.

"RBT1 function" refers to an activity or characteristic associated with expression of RBT1. The nature of this activity(s) or characteristic(s) appears to stem from association with TUP1 function and/or morphological transition. These functions include, but are not limited to, (a) transcription; (b) translation; (c) regulation by TUP1, particularly up-regulated when TUP1 finction is compromised; (d) regulated during conversion (i.e., induction) between morphological forms, particularly up-regulated during conversion into filamentous form; (e) regulated during maintenance of the filamentous form.

As used herein, a characteristic which is associated with a "modulation of RBT1 function" is a characteristic which is associated with an alteration, increase or decrease, in RBT1 function.

As used herein, a characteristic which is associated with a "compromise of RBT1 function" is a characteristic which is associated with a decrease in RBT1 function. This decrease may range from partial to total loss, or knockout, of RBT1 function. Characteristics associated with a compromise of RBT1 function depend upon the organism for which this is being assessed and will be discussed in detail below. Compromise of RBT1 finction can occur as a result of an effect at any point along any pathway in which RBT1 is involved, from transcription of the RBT1 gene, to RBT1 expression (i.e., transcription and/or translation), to the half-life and/or stability of Rbt1, to activity associated with Rbt1.

A polypeptide or polynucleotide (used interchangeably in this context) that "complements" an rbt1 mutation in a yeast cell substitutes for, or provides, a finction of RBT1. An "rbt1" mutation uses standard terminology in the art and refers to a mutation in the RBT1 gene, which may impart either partial to total loss of RBT1 function. Complementation is a term well-understood in the art, and as used herein refers to the ability of a polynucleotide (via its encoded polypeptide) to restore at least one finction associated with wild type RBT1.

As used herein, "TUP1" or "TUP1 gene" refers to the C. albicans TUP1 gene described herein. "Tup1" refers to a protein (polypeptide) product encoded in the C. albicans TUP1 gene. "TUP1 function" refers to an activity or characteristic associated with expression of TUP1. The nature of this activity(s) or characteristic(s) appear to stem from regulation of certain genes. As used herein, a characteristic which is associated with a "compromise of TUP1 function" is a characteristic which is associated with a decrease in TUP1 function.

As used herein, a "polynucleotide" is a polymeric form of nucleotides of any length, which contain deoxyribonucleotides, ribonucleotides, and/or their analogs. The terms "polynucleotide" and "nucleotide" as used herein are used interchangeably. Polynucleotides may have any three-dimensional structure, and may perform any finction, known or unknown. The term "polynucleotide" includes double-, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form. Not all linkages in a polynucleotide need be identical.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, primers, and adaptors. A polynucleotide may comprise modified nucleotides, such as methylated nucleotides and nucleotide analogs. The use of uracil as a substitute for thymine in a deoxyribonucleic acid is also considered an analogous form of pyrimidine.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide. A "partial sequence" is a linear sequence of part of a polynucleotide which is known to comprise additional residues in one or both directions.

If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications included in this definition are, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for exanple, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., α-anomeric nucleic acids, etc.), as well as unmodified forms of the polynucleotide(s).

Further, any of the hydroxyl groups ordinarily present in the sugars may be replaced by phosphonate groups, phosphate groups, protected by standard protecting groups, or activated to prepare additional linkages to additional nucleotides, or may be conjugated to solid supports. The 5' and 3' terminal OH groups can be phosphorylated or substituted with amines or organic capping group moieties of from 1 to 20 carbon atoms. Other hydroxyls may also be derivatized to standard protecting groups.

Polynucleotides can also contain analogous forms of ribose or deoxyribose sugars that are generally known in the art, including, but not limited to, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside.

Although conventional sugars and bases will be used in applying the method of the invention, substitution of analogous forms of sugars, purines and pyrimidines can be advantageous in designing a final product, as can alternative backbone structures like a polyamide backbone.

A polynucleotide or polynucleotide region has a certain percentage (for example, 75%, 80%, 85%, 90%, or 95%) of "sequence identity" to another sequence means that, when aligned, that percentage of bases are the same in comparing the two sequences.

A "primer" is a short polynucleotide, generally with a free 3'-OH group, that binds to a target potentially present in a sample of interest by hybridizing with the target, and thereafter promoting polymerization of a polynucleotide complementary to the target.

An "adaptor" is a short, partially-duplexed polynucleotide that has a blunt, double-stranded end and a protruding, single-stranded end. It can be ligated, through its double-stranded end, to the double-stranded end of another polynucleotide. This provides known sequences at the ends of thus modified polynucleotides. Often adaptors contain specific sequences for primer binding and/or restriction endonuclease digestion.

A "probe" when used in the context of polynucleotide manipulation refers to a polynucleotide which is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and enzymes.

"Transformation" or "transfection" refers to the insertion of an exogenous polynucleotide into a host cell, irrespective of the method used for the insertion, for example, lipofection, transduction, infection or electroporation. The exogenous polynucleotide may be maintained as a non-integrated vector, for example, a plasmid, or alternatively, may be integrated into the host cell genome.

A polynucleotide is said to "encode." a polypeptide if, in its native state or when manipulated by methods well known to those skilled in the art, it can be transcribed and/or translated to produce the polypeptide or a fragment thereof. For purposes of this invention, and to avoid cumbersome referrals to complementary strands, the anti-sense (or complementary) strand of such a polynucleotide is also said to encode the sequence; that is, a polynucleotide sequence that "encodes" a polypeptide includes both the conventional coding strand and the complementary sequence (or strand).

The terms "polypeptide", "oligopeptide", "peptide" and "protein" are used interchangeably herein to refer to polymers of amino acids of any length. The polymer may be linear or branched, it may comprise modified amino acids, it may be interrupted by non-amino acids, and it may be assembled into a complex of more than one polypeptide chain. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In the context of polypeptides, a "linear sequence" or a "sequence" is an order of amino acids in a polypeptide in an N-tenninal to C-terminal direction in which residues that neighbor each other in the sequence are contiguous in the primary structure of the polypeptide. A "partial sequence" is a linear sequence of part of a polypeptide which is known to comprise additional residues in one or both directions.

A polypeptide "fragment" (also called a "region") of Rbt1 (or a "Rbt1 fragment" or "Rbt1 region") is a polypeptide comprising an amino acid sequence of Rbt1 that has at least 5 contiguous amino acids of a sequence of Rbt1, more preferably at least 10 contiguous amino acids, more preferably at least about 15 contiguous amino acids, even more preferably at least about 25 contiguous amino acids, even more preferably at least about 30 contiguous amino acids, even more preferably at least about 40 contiguous amino acids. An Rbt1 fragment may be characterized as having any of the following functions: (a) ability to elicit a humoral and/or cellular immune response; (b) regulated by TUP1 (more particularly, expression up-regulated when TUP1 function is compromised and repressed upon normal TUP1 finction), (c) expressed upon induction to filamentous growth. It is understood that, in this context, an Rbt1 fragment that is "regulated" or "expressed" means that a polypeptide containing a sequence corresponding to the Rbt1 fragment (i.e., having at least 75%, preferably 80%, preferably 85%, preferably 90%, more preferably 95%, more preferably 100% sequence identity) is regulated or expressed. Further finctional attributes of Rbt1 (and Rbt1 fragments) may be characterized based on Rbt1's association with TUP1 finction, particularly morphological transition and the maintenance of the filamentous form. For example, over-expression of RBT1 may induce transition to filament formation. Compromise (including complete loss) of RBT1 function may be correlated with certain phenotypes, such as growth requirements and cell shape, or inability to form filaments, or reduced infectivity. An Rbt1 fragment may also be able to be identified by its ability to complement an rbt1 mutation. Any of these functions may be a basis for identifying and characterizing Rbt1 polypeptide fragments.

A "fusion polypeptide" is a polypeptide comprising regions in a different position than occurs in nature. The regions may normally exist in separate proteins and are brought together in the fusion polypeptide, or they may normally exist in the same protein but are placed in a new arrangement in the fusion polypeptide.

A "functionally preserved" variant of an RBT1 polynucleotide or Rbt1 polypeptide is an RBT1 or Rbt1 sequence which retains at least one aspect of RBT1 finction. Functionally preserved variants can be due to differences in linear sequence, arising from, for example, single base mutation (s), addition(s), deletion(s), and/or modification(s) of the bases. The difference can also arise from changes in the sugar(s) and/or linkage(s) between the bases. Regarding polypeptides, functionally preserved variants may arise, for example, by conservative and/or non-conservative amino acid substitutions, amino acid analogs, and deletions. The finction that is preserved depends upon the relevant function being considered. For example, if an RBT1 polynucleotide is considered for a probe, then the ability of a variant polynucleotide sequence to hybridize to the target is the relevant function. If a polynucleotide is considered for its ability to encode an Rbt1 polypeptide (or fragment thereof), then the ability of a variant sequence to encode the same polypeptide is the relevant function. If an Rbt1 polypeptide is considered for its ability to bind to a particular entity (such as an antibody), then the ability of a variant sequence to encode a polypeptide with equivalent binding characteristics that is relevant.

"Recombinant," as applied to a polynucleotide or gene, means that the polynucleotide is the product of various combinations of cloning, restriction and/or ligation steps, and other procedures that result in a construct that is distinct from a polynucleotide found in nature.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA. Also included are vectors that provide more than one of the above functions.

"Expression vectors" are defined as polynucleotides which, when introduced into an appropriate host cell, can be transcribed and translated into a polypeptide(s). An expression vector also comprises control elements operatively linked to the encoding region to enable and/or facilitate expression of the polypeptide in the target cell. An "expression system" usually connotes a suitable host cell comprised of an expression vector that can function to yield a desired expression product.

A "host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

A "cell line" or "cell culture" denotes eukaryotic cells, derived from higher, multicellular organisms, grown or maintained in vitro. It is understood that the descendants of a cell may not be completely identical (either morphologically, genotypically, or phenotypically) to the parent cell. Cells described as "uncultured" are obtained directly from a living organism, and are generally maintained for a limited amount of time away from the organism (i.e., not long enough or under conditions for the cells to undergo substantial replication).

As used herein, "expression" includes transcription and/or translation.

A "biological sample" encompasses a variety of sample types obtained from an individual and can be used in a diagnostic or monitoring assay. The definition encompasses blood and other liquid samples of biological origin, solid tissue samples such as a biopsy specimen, tissue cultures or cells derived therefrom, and the progeny thereof and sections or smears prepared from any of these sources. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

"Heterologous" means derived from (i.e., obtained from) a genotypically distinct entity from the rest of the entity to which it is being compared. For example, a polynucleotide may be placed by genetic engineering techniques into a plasmid or vector derived from a different source, thus becoming a heterologous polynucleotide. A promoter which is linked to a coding sequence with which it is not naturally linked is a heterologous promoter.

An "isolated" or "purified" polynucleotide, polypeptide, antibody or cell is one that is substantially free of the materials with which it is associated in nature. By substantially free is meant at least 50%, preferably at least 70%, more preferably at least 80%, and even more preferably at least 90% free of the materials with which it is associated in nature. As used herein, an "isolated" polynucleotide or polypeptide also refers to recombinant polynucleotides or polypeptides, which, by virtue of origin or manipulation: (1) are not associated with all or a portion of a polynucleotide or polypeptide with which it is associated in nature, (2) are linked to a polynucleotide or polypeptide other than that to which it is linked in nature, or (3) does not occur in nature, or (4) in the case of polypeptides arise from expression of recombinant polynucleotides. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

A "reagent" polynucleotide, polypeptide, or antibody, is a substance provided for a reaction, the substance having some known and desirable parameters for the reaction. A reaction mixture may also contain a "target", such as a polynucleotide, antibody, polypeptide, or assembly of polypeptides that the reagent is capable of reacting with. For example, in some types of diagnostic tests, the presence and/or amount of the target in a sample is determined by adding a reagent, allowing the reagent and target to react, and measuring the amount of reaction product (if any). In the context of clinical management, a "target" may also be a cell, collection of cells, tissue, or organ that is the object of an administered substance, such as a pharmaceutical compound.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PCR, or the enzymatic cleavage of a polynucleotide by a ribozyme.

When hybridization occurs in an antiparallel configuration between two single-stranded polynucleotides, those polynucleotides are described as "complementary". A double-stranded polynucleotide can be "complementary" to another polynucleotide if hybridization can occur between one of the strands of the first polynucleotide and the second. Complementarity (the degree that one polynucleotide is complementary with another) is quantifiable in terms of the proportion of bases in opposing strands that are expected to form hydrogen bonding with each other, according to generally accepted base-pairing rules.

A "stable duplex" of polynucleotides, or a "stable complex" formed between any two or more components in a biochemical reaction, refers to a duplex or complex that is sufficiently long-lasting to persist between formation of the duplex or complex and subsequent detection, including any optional washing steps or other manipulation that may take place in the interim.

A substance is said to be "selective" or "specific" if it reacts or associates more frequently, more rapidly, with greater duration and/or with greater affinity with a particular cell or substance than it does with alternative cells or substances. An antibody "specifically binds" to a target if it binds with greater affinity, avidity, more readily, and/or with greater duration than it binds to other substances.

As used herein, the term "agent" means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds for screening, such as plant or animal extracts, and the like. Compounds can be tested singly or in combination with one another.

As used herein, "naturally occurring," "native," or "wild type" refers to endogenous C. albicans polynucleotides and the C. albicans protein(s) expressed thereby, including alleles and allelic forms of the protein(s). These terms include full-length and processed polynucleotides and polypeptides. Processing can occur in one or more steps, and these terms encompass all stages of processing. For instance, polypeptides having or lacking a signal sequence are encompassed by the invention. "Non-naturally occurring", "non-native", or "non-wild type" refer to all other C. albicans polynucleotides and polypeptides.

A "polymerase chain reaction" ("PCR") is a reaction in which replicate copies are made of a target polynucleotide using one or more primers, and a catalyst of polymerization, such as a reverse transcriptase or a DNA polymerase, and particularly a thermally stable polymerase enzyme. Methods for PCR are taught in U.S. Pat. No. 4,683,195 (Mullis) and U.S. Pat. No. 4,683,202 (Mullis et al.). All processes of producing replicate copies of the same polynucleotide, such as PCR or gene cloning, are collectively referred to herein as "replication."

"Virulence" is a term well understood in the art and means an ability to invade, infect, multiply, spread, and/or colonize host to the detriment of the host. "Virulence" and "pathogenicity" and "infectivity" are used interchangeably herein. An agent which may control virulence in C. albicans is one which is selected by the screening methods described herein and may, upon further study, prove to control C. albicans virulence and may even exert therapeutic activity.

An "individual" is a vertebrate, preferably a mammal, more preferably a human. Mammals include, but are not limited to, farm animals, sport animals, and pets.

A "vaccine" is a pharmaceutical composition for human or animal use, which is administered with the intention of conferring the recipient with a degree of specific immunological reactivity, or immune response, against a particular target, or group of targets. The immunological reactivity may be antibodies or cells (particularly B cells, plasma cells, T helper cells, and cytotoxic T lymphocytes and their precursors) that are immunologically reactive against the target or any combination thereof. For purposes of this invention, the target is Rbt1 polypeptide(s) (whether full length or functional fragment thereof). Immunological reactivity may be desired for experimental purposes, for treatment, or for the elimination of a particular substance.

An "antibody" (interchangeably used in plural form) is an immunoglobulin molecule capable of specific binding to a target, such as a polypeptide, through at least one antigen recognition site, located in the variable region of the immunoglobulin molecule. An antibody can be from any source of animal capable of producing them, for example, mouse, rat, rabbit, or human antibodies. As used herein, the term encompasses not only intact antibodies, but also fragments thereof (such as Fab, Fab', F(ab')$_2$, Fv, single chain (ScFv)), mutants thereof, fusion proteins, humanized antibodies, and any other modified configuration of the immunoglobulin molecule that comprises an antigen recognition site of the required specificity. The term "antibody" includes polyclonal antibodies and monoclonal antibodies.

"Immunological recognition" or "immunological reactivity" refers to the specific binding of a target through at least one antigen recognition site in an immunoglobulin or a related molecule, such as a B cell receptor or a T cell receptor.

The term "antigen" refers to the target molecule that is specifically bound by an antibody through its antigen recognition site. The antigen may, but need not be chemically related to the immunogen that stimulated production of the antibody. The antigen may be polyvalent, or it may be a monovalent hapten. Examples of kinds of antigens that can be recognized by antibodies include polypeptides, polynucleotides, other antibody molecules, oligosaccharides, complex lipids, drugs, and chemicals.

An "immunogen" is an antigen capable of stimulating production of an antibody when injected into a suitable host, usually a mammal. Compounds may be rendered immunogenic by many techniques known in the art, including crosslinking or conjugating with a carrier to increase valency, mixing with a mitogen to increase the immune response, and combining with an adjuvant to enhance presentation.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as: "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., 1991).

For techniques related to C. albicans and other yeast, see, inter alia, *Guide to Yeast Genetics and Molecular Biology*, Guthrie and Fink (eds.) (1991) Vol. 194; Fonzi et al. (1993) *Genetics* 134: 717–728 and references therein.

Basisfor Identification and Description of
Thepolynucleofide and Polypeptide of this
Invention The polynucleotide depicted in SEQ ID NO:1 was identified based on association with a particular biological finction, namely, C. albicans TUP1 finction, more particularly, repression of gene expression by C. albicans TUP1. This polynucleotide (and polypeptide encoded thereby, depicted in SEQ ID NO:2) were further identified by association of their expression with morphological transition, particularly, induction and/or maintenance of filamentous growth. The polynucleotide and polypeptide described herein were discovered and identified according to both of the following criteria.

Cloning Sequences that are Transcribed and/or Upregulated in *C. albicans* Cells Lacking TUP1 Function Compared to *C. albicans* Cells Retaining TUP1 Function A method based on cDNA representational difference analysis (cDNA-RDA) was used to identify and recover polynucleotide sequences specifically expressed in the absence of TUP1 finction. Lisitsyn et. al. (1993) *Science* 259: 946–951; Hubank et al. (1994) *Nucleic Acids Res*. 22: 5640–5648; U.S. Pat. Nos. 5,436,142 and 5,501,964; Lisitsyn et al. (1995) *Meth. Enz.* 254:291–304. Briefly, cDNA-RDA is the differential cloning of genes that are transcribed in one type of cell (or under one set of conditions) but not in a different type of cell (or under another set of conditions). Subtractive hybridization between two cDNA populations, one from cells lacking TUP1 function and the other from wild type TUP1 cells, removes the sequences in common (here, sequences not regulated by the TUP1 gene product). The non-common DNA sequences are then selectively amplified by PCR. The amplified polynucleotide sequences are thus associated with genes repressed by the TUP1 gene.

Generally, for this method, cDNA was synthesized from the mRNA of tup1 mutant cells and the 5' and 3' ends of the cDNA were modified by the addition of specific polynucleotide adaptors. This cDNA was hybridized, in two sequential reactions, with excess, unmodified cDNA made from the mRNA of cells with wild type TUP1 finction. These reactions resulted in the hybridization of complementary polynucleotide sequences common to both populations and the enrichment of sequences with modified ends from tup1 mutant cells. With the use of PCR and polynucleotide primers directed at the modified ends, the desired sequences were selectively amplified from the mixture of sequences in the hybridization reaction. The PCR products were then inserted into appropriate cloning vectors. A PCR-Select™ cDNA Subtraction Kit from Clontech Laboratories, Inc. was used to perform the cDNA-RDA. A more detailed description of this technique is provided in Example 1.

To determine whether the cloned cDNAs represented mRNAs that are differentially expressed in cells with and without TUP1 function, randomly picked clones were used to probe RNA blots from tup1 mutant cells and wild type cells. RBT1 had increased expression in tup1 mutant cells and so appears to be transcriptionally repressed in the presence of TUP1 function (compare FIG. 1A (wild type TUP1) with FIG. 1B (mutant tup1Δ)).

TUP1 control over RBT1 expression was also tested in a specially engineered strain of *C. albicans* in which TUP1 expression was under control of a maltose-regulated promoter. Braun et al. (1997). Upon shifting the cells from maltose to glucose as the sole carbon source, the TUP1 expression is turned off and the RBT1 expression is rapidly induced (FIG. 1C; Example 2). This rapid induction of RBT1 expression upon depletion of TUP1 function suggests a direct control of RBT1 expression by TUP1.

The TUP1 gene appears to be a repressor of filamentous growth (and/or repressor of morphological transition from blastospore to filament) since, in the absence of TUP1 function, *C. albicans* grows exclusively in filaments. Exposure of wild type *C. albicans* to mammalian serum can also induce filamentous growth. To assay whether the sequence of the identified TUP1-regulated clone was expressed during growth in serum, the cDNA was used to probe a blot of RNA from *C. albicans* grown in the presence of 10% calf serum. Expression of RBT1 was increased in the presence of serum (FIG. 1D). A more detailed description is provided in Example 2.

The *C. albicans* transition to growth in filaments can also be induced on the defmed medium developed by Lee et al. (1975) at pH 7.0. Lee et al. (1975) *Sabouraudia* 13:148. Wild type cells grown in such conditions also up-regulate RBT1 expression.

Thus, using the criteria of both TUP1-repression and induction to filamentous growth (by serum stinulation and by Lee's medium, pH 7.0), RBT1 expression was found to be associated with *C. albicans* TUP1 finction and morphological transition to filamentous growth (FIGS. 1A–D).

The polynucleotide sequence of the fragment of the RBT1 gene recovered in the cDNA cloned is indicated in FIG. 2A and in SEQ ID NO:1. The corresponding partial polypeptide sequence encoded within the RBT1 gene (i.e., a fragment of Rbt1) is indicated in FIG. 2B and in SEQ ID NO:2.

An RBT1 cDNA containing SEQ ID NO: 1 was used as a hybridization probe to recover a λ clone from a *C. albicans* genomic library. One of the clones recovered was found to contain a long open reading frame that when translated, included the Rbt1 polypeptide sequence of FIG. 2B (SEQ ID NO:2). This open reading frame is likely to encode the entire Rbt1 polypeptide since it is a continuous open reading frame from a potential signal sequence (see below) to a translation termination codon. The polynucleotide sequence of the genomic clone of the RBT1 gene is indicated in FIG. 3A and in SEQ ID NO:3. The corresponding polypeptide sequence encoded within the RBT1 gene is indicated in FIG. 3B and in SEQ ID NO:4.

Sequence data of the polynucleotide and polypeptide thus obtained was compared to sequences in GenBank using BLAST searches. Both the RBT1 polynucleotide of SEQ ID NO:1 and the Rbt1 polypeptide of SEQ ID NO:2 are similar to those of the *C. albicans* hyphal wall protein 1 (HWP1) gene. Staab et. al. (1996) *J. Biol. Chem.* 271: 6298–6305. When the RBT1 and HWP1 sequences are aligned using GCG, Inc. sofiware, the RBT1 polynucleotide sequence has 66% identity to the comparable region of HWP1 polynucleotide sequence and the Rbt1 polypeptide sequence has 56% identity to the comparable region of the Hwp1 protein. When the entire Rbt1 polypeptide sequence (SEQ ID NO:4) is aligned with that of Hwp1, the two polypeptides share 44% identity. Despite their similarity, RBT1 is not HWP1 since another clone identified in the TUP1-regulated gene screen was HWP1.

The identification of both RBT1 and HWP1 cDNAs through this two-step process (i.e. screening a cDNA library enriched for sequences repressed by TUP1 for those clones expressed during serum stimulation) confirmed that this approach is a valid way to identify genes expressed during filamentous growth and associated with morphological transition.

HWP1 and RBT1 may be members of a family. Rbt1 and Hwp1 contain a repeated sequence that is also shared with the *S. cerevisiae* protein Flo11 (also known as Muc1). Lambrechts et al. (1996) *Proc. Natl. Acad Sci. USA* 93: 8419–8424; Lo et al. (1996) *J. Bacteriol.* 178: 7144–7151. Hwp1 and Flo11/Muc1 are cell surface proteins. Like RBT1, HWP1 is expressed in *C. albicans* only during filamentous growth. Flo11/Muc1 is required for induction of filamentous growth in *S. cerevisiae* since cells without an intact MUC1 gene were unable to differentiate into pseudohyphae. Lambrechts et al. (1996).

The Hwp1 protein is located on the surface of the hyphal filaments both in laboratory cultures and in tissues of infected hosts. Staab et al. (1996). Although the function of Hwp1 protein is unknown, Staab et al. suggest it may play a role in the interaction between *C. albicans* and host cells. The Flo11 protein is important in cell—cell interaction since its results in the aggregation of *S. cerevisiae* cells in a process known as flocculation. Disruption of the FLO11 gene abolishes flocculation. Lo et al. (1996). The similarity of Rbt1 to Hwp1 and to Flo11 leads to the suggestion that Rbt1 is on the surface of *C. albicans* hyphae in a position to interact with surrounding cells and/or host tissues.

The repeated amino acid sequences of Rbt1, Hwp1, and Flo11/Muc1 are relatively rich in proline residues. In proteins containing such repeats, the prolines are proposed to finction in the maintenance of an extended conformation of the protein and to participate in the noncovalent interactions between the proteins and other molecules. Williamson (1994) *Biochem J.* 297: 249–260. Repetitive surface proteins appear to be the means of many microorganisms to attach to host cells and to evade the host's immune system. Research into mechanisms of *C. albicans*-host interactions has implicated acidic proline-rich proteins on the surface of *C. albicans* in adhesion to oral epithelial cells. Bradway et al. (1993) *Crit. Rev. Oral Biol. Med.* 4: 293–299. The expression of such proteins appeared to increase following the morphological transition from yeast to hyphal form. Like Rbt1 and Hwp1, the acidic proline-rich proteins used by Bradway et al. (1993) contain glutamic acid residues within the proline-rich repeats. The repeated amino acid sequences of Rbt1 and Hwp1 are located in the carboxy-terminal half of the proteins.

Rbt1 and Hwp1 also share a similar amino (N-) terminus. When aligned, the N-terminal 23 amino acids of Rbt1 and Hwp1 are 65% identical. As Hwp1 is expressed on the cell surface, this N-terminus may be a signal sequence that promotes the processing and/or secretion of the polypeptide bearing it.

Polynucleotides of the Invention

The present invention provides RBT1 polynucleotides from *C. albicans* that are associated with *C. albicans* TUP1 function (namely, repression of gene expression), with morphological transition, namely, transition from blastospore to filamentous growth, and with filamentous growth per se. It encompasses RBT1 polynucleotides encoding *C. albicans* Rbt1 (i.e., Rbt1 polypeptides), 5' and 3' flanking regions of the RBT1 gene, vectors containing these polynucleotides, host cells containing these polynucleotides, and compositions comprising these polynucleotides. These polynucleotides are isolated and/or produced by chemical and/or recombinant methods, or a combination of these methods. Unless specifically stated otherwise, "polynucleotides" shall include all embodiments of the polynucleotides of this invention. These polynucleotides are useful as probes, primers, in expression systems, and in screening methods as described herein.

The cloning of RBT1 polynucleotide sequence is described in Example 1. Accordingly, this invention provides an isolated polynucleotide that contains a sequence encoding an Rbt1 polypeptide from *C. albicans* wherein the polypeptide is at least 10 amino acids in length and is depicted in SEQ ID NO:2 or SEQ ID NO:4.

In another embodiment, this invention provides an isolated polynucleotide that encodes an Rbt1 polypeptide from about amino acid 480 to about amino acid 496 of SEQ ID NO:4. In other embodiments, this invention includes an isolated polynucleotide that encodes an Rbt1 polypeptide from about amino acid 365 to about amino acid 397, about amino acid 348 to about amino acid 397, about amino acid 331 to about amino acid 397, or about amino acid 308 to about amino acid 397 of SEQ ID NO:4. In other embodiments, this invention includes an isolated polynucleotide that encodes an Rbt1 polypeptide from about amino acid 628 to about amino acid 672, about amino acid 599 to about amino acid 672, or about amino acid 580 to about amino acid 672 of SEQ ID NO:4. In one embodiment, the invention includes an isolated polynucleotide that encodes an Rbt1 polypeptide from about amino acid 1 to about amino acid 17 of SEQ ID NO:2. These embodiments encompass proline-rich repeat regions, discussed above.

In another embodiment, this invention provides an isolated polynucleotide sequence that encodes an Rbt1 polypeptide from about amino acid 1 to about amino acid 23 of SEQ ID NO:4. This embodiment encompasses the amino terminus region (discussed above) which may function as a signal sequence for polypeptide processing and/or secretion.

In another embodiment, the Rbt1 polypeptide encoded within the polynucleotide is the sequence of SEQ ID NO:2.

In another embodiment, the Rbt1 polypeptide encoded within the polynucleotide is the sequence of SEQ ID NO:4.

In another embodiment, the invention includes an isolated polynucleotide comprising nucleotides from about 2054 to about 2104 of SEQ ID NO:3. In other embodiments, this invention includes an isolated polynucleotide comprising nucleotides from about 1709 to about 1807, about 1668 to about 1807, about 1607 to about 1807, or about 1538 to about 1807 of SEQ ID NO:3. In other embodiments, this invention includes an isolated polynucleotide comprising nucleotides from about 2498 to about 2632, about 2411 to about 2632, or about 2354 to about 2632 of SEQ ID NO:3.

In another embodiment, the invention includes an isolated polynucleotide comprising nucleotides from about 617 to about 685 of SEQ ID NO:3.

This invention also provides an isolated polynucleotide that contains a sequence encoding Rbt1 comprising nucleotides from about 617 to about 2866 of SEQ ID NO:3.

The invention includes modifications to the RBT1 polynucleotides described above such as deletions, substitutions, additions, or changes in the nature of any nucleic acid moieties. A "modification" is any difference in nucleotide sequence as compared to a polynucleotide shown herein to encode an Rbt1 polypeptide, and/or any difference in terms of the nucleic acid moieties of the polynucleotide(s). Such changes can be useful to facilitate cloning and modifying expression of RBT1 polynucleotides. Such changes also can be useful for conferring desirable properties to the polynucleotide(s), such as stability. The definition of polynucleotide provided herein gives examples of these modifications. Hence, the invention also includes finctionally-preserved variants of the nucleic acid sequences disclosed herein, which include nucleic acid substitutions, additions, and/or deletions.

The invention also encompasses RBT1 polynucleotides including full-length (unprocessed), processed, coding, noncoding (including flanking region) or portions thereof, provided that these polynucleotides contain a region encoding at least a portion of Rbt1. Also embodied are the mRNA and cDNA sequences and fragments thereof that include a portion Rbt1 encoding segment.

The invention also encompasses polynucleotides encoding for functionally equivalent variants and derivatives of full-length Rbt1 and functionally equivalent fragments thereof which may enhance, decrease or not significantly affect properties of the polypeptides encoded thereby. For instance, changes in a DNA sequence that do not change the encoded amino acid sequence, as well as those that result in conservative substitutions of amino acid residues, non-deleterious non-conservative substitutions, one or a few amino acid deletions or additions, and substitution of amino acid residues by amino acid analogs are those which will not significantly affect properties of the encoded polypeptide. Nucleotide substitutions that do not alter the amino acid residues encoded can be useful for optimizing gene expression in different systems. Suitable substitutions are known to those of skill in the art and are made, for instance, to reflect preferred codon usage in the particular expression systems. In another example, alternatively spliced polynucleotides can give rise to a functionally equivalent fragment or variant of Rbt1. Alternatively processed polynucleotide sequence variants are defined as polynucleotide sequences corresponding to mRNAs that differ in sequence for one another but are derived from the same genomic region, for example, mRNAs that result from: 1) the use of alternative promoters; 2) the use of alternative polyadenylation sites; and/or 3) the use of alternative splice sites.

The RBT1 polynucleotides of the invention also include polynucleotides encoding other Rbt1 fragments. The polynucleotides encoding Rbt1 fragments are useful, for example, as probes, therapeutic agents, a polypeptide processing signal, and as a template for encoding various functional domains of Rbt1. Accordingly, the invention includes a polynucleotide that comprises a region of at least 15 contiguous nucleotides, more preferably at least about 20 contiguous nucleotides, more preferably at least about 25 contiguous nucleotides, more preferably at least about 35 contiguous nucleotides, more preferably at least about 50 contiguous nucleotides, even more preferably at least about 75 contiguous nucleotides, even more preferably at least about 100 contiguous nucleotides, even more preferably at least about 200 contiguous nucleotides, even more preferably at least about 300 contiguous nucleotides.

Another embodiment of the invention is isolated polynucleotides comprising a region of at least 20 contiguous nucleotides, with the region having at least 75% sequence identity with a sequence depicted in SEQ ID NO:3 or SEQ ID NO:1. Alternatively, the region may also have 85% sequence identity, preferably 90% sequence identity, preferably 95% sequence identity, more preferably 97% sequence identity. Further, the expression of a polynucleotide containing this region is increased during conversion of C. albicans to filamentous form and is regulated by TUP1 in C. albicans. Further, the invention includes polynucleotides comprising longer regions having at least 80%, preferably 85%, preferably 90%, preferably 95%, more preferably 97% sequence identity with a sequence depicted in SEQ ID NO:3 or SEQ ID NO:1. Alternatively, these regions may comprise at least 25 contiguous nucleotides, 30 contiguous nucleotides, 50 contiguous nucleotides, 60 contiguous nucleotides, 75 contiguous nucleotides, or 100 contiguous nucleotides.

In terms of hybridization conditions, the higher the sequence identity required, the more stringent are the hybridization conditions if such sequences are determined by their ability to hybridize to a sequence of SEQ ID NO:1 or SEQ ID NO:3. Accordingly, the invention also includes polynucleotides that are able to hybridize to a sequence comprising at least 20 contiguous nucleotides (or more, such as 25, 35, 50, 75 or 100 contiguous nucleotides) of SEQ ID NO:1 or SEQ ID NO:3. The hybridization conditions would be stringent, i.e., 80° C. (or higher temperature) and 6×SSC (or less concentrated SSC). A discussion regarding hybridization reactions follows.

Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where 1×SSC is 0.15 M NaCl and 15 mM citrate buffer) and their equivalents using other buffer systems; formamide concentrations of 0%, 25%, 50%, and 75%; incubation times from 24 hours to 5 minutes; 1, 2, or more washing steps; wash incubation times of 1, 2, or 15 minutes; and wash solutions of 6×SSC, 1×SSC, 0.1×SSC, or deionized water.

"$T_m$" is the temperature in degrees Centigrade at which 50% of a polynucleotide duplex made of complementary strands hydrogen bonded in anti-parallel direction by Watson-Crick base pairing dissociates into single strands under conditions of the experiment. $T_m$ may be predicted according to a standard formula, such as:

$$T_m = 81.5 + 16.6 \log[X^+] + 0.41\ (\%G/C) - 0.61(\%F) - 600/L$$

where [$X^+$] is the cation concentration (usually sodium ion, $Na^+$) in mol/L; (%G/C) is the number of G and C residues as a percentage of total residues in the duplex; (%F) is the percent formamide in solution (wt/vol); and L is the number of nucleotides in each strand of the duplex.

Compositions containing RBT1 polynucleotides are encompassed by this invention. The invention also provides compositions comprising a vector(s) containing an RBT1 polynucleotide as well as compositions comprising a host cell containing an RBT1 polynucleotide, as described herein. When these compositions are to be used pharmaceutically, they are combined with a pharmaceutically acceptable excipient.

Preparation of RBT1 polynucleotides of this invention

The polynucleotides of this invention can be obtained using chemical synthesis, recombinant methods, or PCR.

Methods of chemical polynucleotide synthesis are well known in the art and need not be described in detail herein. One of skill in the art can use the sequences provided herein and a commercial DNA synthesizer to produce a desired DNA sequence.

For preparing RBT1 polynucleotides using recombinant methods, a polynucleotide comprising a desired sequence can be inserted into a suitable vector, and the vector in turn can be introduced into a suitable host cell for replication and amplification. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as *PCR: The Polymerase Chain Reaction*, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example. RNA can also be obtained through in vitro reactions. For example, the RBT1 polynucleotide can be inserted into a vector that contains appropriate transcription promoter sequences. Commercially available RNA polymerases will specifically initiate transcription at their promoter sites and continue the transcription process through the adjoining DNA polynucleotides. Placing the RBT1 polynucleotides between two such promoters allows the generation of sense or antisense strands of RBT1 RNA.

If used as a vaccine (i.e., pharmaceutical composition for eliciting an immune response), plasmids containing RBT1 polynucleotides are preferably prepared as described by Horn et al. ((1995) *Human Gene Therapy* 6:565–573) which produces a pharmaceutical grade plasmid DNA suitable for administration.

Cloning and expression vectors comprising RBT1 polynucleotide

The present invention further includes a variety of vectors containing RBT1 polynucleotides of this invention. These vectors can be used for expression of recombinant polypeptides as well as a source of RBT1 polynucleotides. Cloning vectors can be used to obtain replicate copies of the RBT1 polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express Rbt1 polypeptides in an individual, such as for eliciting an immune response via the polypeptide(s) encoded in the expression vector(s). Suitable cloning and expression vectors include any known in the art, e.g., those for use in in vitro, bacterial, mammalian, yeast and insect expression systems. Specific vectors and suitable host cells are known in the art and need not be described in detail herein. For example, see Gacesa and Ramji, *Vectors*, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins substances, e.g., ampicillin, neomycin, methotrexate, etc.; (b) complement auxotrophic deficiencies; or (c) supply critical nutrients not available from complex media. The choice of the proper marker gene will depend on the host cell, and appropriate genes for different hosts are known in the art. Cloning and expression vectors also typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide encoding an Rbt1 polypeptide of interest. The RBT1 polynucleotide encoding the polypeptide is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) may be derived from the RBT1 gene, or they may be heterologous (i.e., derived from other genes and/or other organisms). A polynucleotide sequence encoding a signal peptide can also be included to allow an Rbt1 polypeptide to cross and/or lodge in cell membranes or be secreted from the cell. A number of expression vectors suitable for expression in eukaryotic cells including yeast, avian, and mammalian cells are known in the art. The examples provided herein contain a number of examples of expression vectors for yeast systems, particularly *S. cerevisiae* and *C. albicans*. For instance, pRD53 can be used for Gal-induced expression in *S. cerevisiae*. Other common vectors, such as YEp13 and the Sikorski series pRS303–306, 313–316, 423–426 can also be used. Vectors pDBV52 and pDBV53 are suitable for expression in *C. albicans*. Another example of an expression vector (system) is the baculovirus/insect cell system. Expression of RBT1 RNA in vitro is described above.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus). The choice of means of introducing vectors or RBT1 polynucleotides will often depend on the host cell.

Host cells transformed with RBT1 polynucleotides

Another embodiment of this invention are host cells transformed with (i.e., comprising) RBT1 polynucleotides and/or vectors having RBT1 polynucleotide(s) sequences, as described above. Both prokaryotic and eukaryotic host cells may be used. Prokaryotic hosts include bacterial cells, for example *E. coli, B. subtilis*, and mycobacteria. Among eukaryotic hosts are yeast, insect, avian, plant and mammalian cells. Host systems are known in the art and need not be described in detail herein. Examples of fungi (including yeast) host cells are *S. cerevisiae, Kluyberomyces lactis* (*K. lactis*), species of Candida including *C. albicans* and *C. glabrata, C. maltosa, C. utilis, C. stellatoidea, C. parapsilosis, C. tropicalus, Neurospora crassa, Aspergillus nidulans, Schizosaccharomyces pombe* (*S. pombe*), *Pichia pastoris*, and *Yarowia lipolytica*.

The host cells of this invention can be used, inter alia, as repositories of RBT1 polynucleotides and/or vehicles for production of RBT1 polynucleotides and/or polypeptides. They may also be used as vehicles for in vivo delivery of Rbt1 polypeptides.

Uses for and methods using RBT1 polynucleotides

The polynucleotides of this invention have several uses. RBT1 polynucleotides are useful, for example, in expression systems for the recombinant production of Rbt1 or Rbt1 fragments. They are useful as hybridization probes to assay for the presence of RBT1 polynucleotide (or related) sequences in a sample using methods well known to those in the art. Further, RBT1 polynucleotides are also useful as primers to effect amplification of desired polynucleotides, and may be useful as probes to obtain other family members which are associated with morphologic transition. They are also useful as indicators of TUP1 function. The RBT1 polynucleotides of this invention may be useful as vaccines.

The RBT1 polynucleotides of this invention can be used in expression systems to produce Rbt1 polypeptides, including recombinant forms, including those which have enhanced, equivalent, or different, desirable properties. These recombinant forms are made by using routine methods in the art. Examples of recombinant forms of Rbt1 polypeptides include, but are not limited to, fusion proteins containing other components. A more detailed description of these recombinant forms of polypeptides and how they are made is provided below.

The RBT1 polynucleotides can also be used as hybridization probes for detection of, for example, the presence of polynucleotides in a cell. For instance, a polynucleotide could be used as a probe to determine the presence of C. albicans polynucleotide sequences in infected cells. For these methods, a suitable cell sample or a sample derived from cells (either of which are suspected of containing C. albicans polynucleotide sequences) is obtained and tested for the presence of RBT1 polynucleotide by contacting the polynucleotides from the sample with the RBT1 polynucleotide probe. The method is conducted to allow hybridization to occur between the probe and polynucleotide of interest, and the resultant (if any) hybridized complex is detected. Such methods entail procedures well known in the art, such as cell culture, polynucleotide preparation, hybridization, and detection of hybrid complexes formed, if any. Using similar methods, the RBT1 probes can also be used to detect vectors which are in turn used to produce intact, recombinant, or variant forms of Rbt1 polypeptides. This use of polynucleotides is discussed in more detail below.

RBT1 polynucleotides of this invention can be used as primers for amplification of polynucleotides encoding RBT1 or a fragment thereof, such as in a PCR, as described above. The conditions for carrying out PCR reactions depend on the specificity desired, which in turn can be adjusted by the primer used and the reaction conditions. Such adjustments are known in the art and need not be discussed in detail herein.

The similarity of RBT1 and HWP1 in sequence and expression pattern suggests that they may be members of a family of genes. Accordingly, the RBT1 polynucleotides can also be used as hybridization probes and/or as primers for amplification reactions to identify and isolate polynucleotides of RBT1-related genes, which may in turn be associated with morphologic transition.

The RBT1 polynucleotides may also be used as indicators of TUP1 function in C. albicans. As described above, TUP1 appears to regulate the expression of RBT1 such that, in the presence of Tup1 protein, RBT1 expression is repressed. In C. albicans cells lacking TUP1 function, expression of RBT1 is upregulated. Accordingly, agents or conditions which compromise TUP1 function may be detected by their ability to cause increase of RBT1 expression and/or ability to elicit filamentous growth. Further, C. albicans lacking TUP1 function have reduced infectivity compared to wild type C. albicans. Since an increase of RBT1 mRNA may indicate a decrease in TUP1 finction, RBT1 polynucleotides may be used to assess the pathogenic potential of a C. albicans strain. They can also be used to monitor the activity of agents that affect TUP1 function.

Another use of the polynucleotides is in vaccines. The general principle is to administer the polynucleotide so that it either promotes or attenuates the expression of the polypeptide encoded therein. Thus, the present invention includes methods of inducing an immune response and methods of treatment comprising administration of an effective amount polynucleotide(s) to an individual. In these methods, a polynucleotide encoding a polypeptide is administered to an individual, either directly or via cells transfected with the polynucleotide(s). Preferably, the polynucleotide is replicated inside a cell. Thus, the polynucleotide(s) is operatively linked to a suitable promoter, such as a heterologous promoter that is intrinsically active in cells of the target tissue type. Entry of the polynucleotide into the cell is accomplished by techniques known in the art, such as via a viral expression vector, such as a vaccinia or adenovirus vector, or association of the polynucleotide with a cationic liposome. Preferably, the polynucleotide(s) are in the form of a circular plasmid, preferably in a supercoiled configuration. Preferably, once in cell nuclei, plasmids persist as circular non-replicating episomal molecules. In vitro mutagenesis can in turn be carried out with the plasmid constructs to encode, for example, more immunogenic molecules or T cell epitopes with a desirable HLA motif.

To determine whether plasmids containing polynucleotides are capable of expression in eukaryotic cells, cells such as, for example, COS-7 (primate origin, CHO (rodent origin), or HeLa (human origin) cells can be transfected with the plasmids. Expression resulting in a polypeptide(s) is then determined by RIA, ELISA, immunofluorescence of fixed cells, or western blotting of cell lysate using an anti-Rbt1 antibody as a probe. Alternatively, expression of smaller polypeptides can be detected, for example, by constructing the plasmid so that the resultant polypeptide is labeled recombinantly, such as with an enzymatic label. Further characterization of the expressed polypeptide can be achieved by purification of the polypeptide using techniques known in the art.

Polypeptides of the Invention

The present invention encompasses C. albicans Rbt1 polypeptide sequences. Expression of Rbt1 is regulated by C. albicans TUP1 function. The polypeptides may comprise any novel region (i.e., not disclosed in the public domain as of the filing date of the original application of this series) of SEQ ID NO:4. Unless specifically stated, the term "polypeptide(s)" shall include all polypeptide embodiments of this invention.

The polypeptides have a variety of uses, including their use as a diagnostic tool for detecting antibodies against C. albicans, their use in making antibodies that bind to these polypeptides, their use as an antigen for vaccines (i.e., pharmaceutical compositions that elicit an immune response in an individual), their use as agents to screen pharmaceutical candidates (both in vitro and in vivo), and their use in rational (i.e., structure-based) drug design. The Rbt1 polypeptides may also be used to identify proteins, especially those of C. albicans, that interact physically with Rbt1 which could thus themselves be drug targets.

The amino acid sequence of Rbt1 is shown in FIG. 3(B) and SEQ ID NO:4. The amino acid sequence of a fragment of Rbt1 is shown in FIG. 2(B) and SEQ ID NO:2.

In one embodiment, the invention includes an isolated polypeptide comprising an Rbt1 polypeptide of C. albicans, wherein the polypeptide comprises about amino acid 480 to about amino acid 496 of SEQ ID NO:4, a proline-rich repeat region. In other embodiments, this invention includes an isolated polypeptide comprising an Rbt1 polypeptide from about amino acid 365 to about amino acid 397, about amino acid 348 to about amino acid 397, about amino acid 331 to about amino acid 397, or about amino acid 308 to about amino acid 397 of SEQ ID NO:4. In other embodiments, this invention includes an isolated polypeptide comprising an Rbt1 polypeptide from about amino acid 628 to about amino acid 672, about amino acid 599 to about amino acid 672, or about amino acid 580 to about amino acid 672 of SEQ ID NO:4. These embodiments encompass proline-rich repeat regions, discussed above.

In one embodiment, the invention includes an isolated polypeptide comprising an Rbt1 polypeptide of C. albicans, wherein the polypeptide comprises about amino acid 1 to about amino acid 17 of SEQ ID NO:2, a proline-rich repeat region.

In another embodiment, the invention includes an isolated polypeptide comprising about amino acid 1 to about amino acid 23 of SEQ ID NO:4.

In another embodiment, the invention includes an isolated polypeptide comprising an Rbt1 polypeptide of C. albicans, wherein the polypeptide comprises the sequence of SEQ ID NO:2. In another embodiment, the invention includes an isolated polypeptide comprising an Rbt1 polypeptide of C. albicans, wherein the polypeptide comprises the sequence of SEQ ID NO:4.

In another embodiment, the invention provides an isolated polypeptide comprising at least 10 contiguous amino acids which have at least 70% sequence identity to a sequence depicted in SEQ ID NO:4. Alternatively, the 10 contiguous amino acids have at least 70% sequence identity to a sequence depicted in SEQ ID NO:2. The expression of said at least 10 contiguous amino acids contained in a polypeptide is increased during conversion of C. albicans to filamentous form.

In one embodiment, the Rbt1 polypeptide referred to above is regulated by TUP1 in C. albicans.

The size of Rbt1 polypeptides may vary widely, as the length required to effect activity could be as small as, for example, a 5-mer amino acid sequence to effect an immune response. The maximum length generally is not detrimental to effecting activity. The minimum size must be sufficient to provide a desired function. Thus, the invention includes polypeptide fragments of Rbt1 comprising a portion of the amino acid sequence depicted in SEQ ID NO:2 in which the Rbt1 polypeptide is about 15, preferably 25, more preferably 50 more preferably 75, more preferably 100 amino acids in length. As is evident to one skilled in the art, these Rbt1 polypeptides, regardless of their size, may also be associated with, or conjugated with, other substances or agents to facilitate, enhance, or modulate function and/or specificity of an Rbt1 polypeptide.

The invention includes modifications to Rbt1 polypeptides including functionally equivalent fragments of the Rbt1 polypeptides which do not significantly affect their properties and variants which have enhanced or decreased activity. Collectively, these modifications may be termed "analogs" of Rbt1 or a fragment of Rbt1. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Such conservative substitutions are known in the art, and preferably, the amino acid substitutions would be such that the substituted amino acid would possess similar chemical properties as that of the original amino acid. These polypeptides also include glycosylated and non-glycosylated polypeptides, as well as polypeptides with other post-translational modifications, such as, for example, glycosylation with different sugars, acetylation, and phosphorylation. Amino acid modifications can range from changing or modifying one or more amino acids to complete redesign of a region. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified Rbt1 polypeptides are made using established procedures in the art and can be screened using standard assays known in the art.

The invention also encompasses fusion proteins comprising one or more Rbt1 polypeptides. For purposes of this invention, an Rbt1 fusion protein contains one or more Rbt1 polypeptides and another amino acid sequence to which it is not attached in the native molecule, for example, a heterologous sequence or a homologous sequence from another region. Useful heterologous sequences include, but are not limited to, sequences that provide for secretion from a host cell, enhance immunological reactivity, or facilitate the coupling of the polypeptide to an immunoassay support or a vaccine carrier. For instance, an Rbt1 polypeptide can be fused with a bioresponse modifier. Examples of bioresponse modifiers include, but are not limited to, cytokines or lymphokines such as GM-CSF, interleukin-2 (IL-2), interleukin 4 (IL-4), and γ-interferon. Accordingly, the invention includes Rbt1 fusion polypeptides that contain GM-CSF or IL-2. Another useful heterologous sequence is one which facilitates purification. Examples of such sequences are known in the art and include those encoding epitopes such as Myc, HA (derived from influenza virus hemagglutinin), His-6, or FLAG. Other heterologous sequences that facilitate purification are derived from proteins such as glutathione S-transferase (GST), maltose-binding protein (MBP), or the Fc portion of immunoglobulin.

The invention also encompasses polymeric forms of Rbt1 polypeptides. As used herein, a polymeric form of an Rbt1 polypeptide contains a plurality (i.e., more than one) of Rbt1 polypeptides. In one embodiment, linear polymers of Rbt1 polypeptides are provided. These Rbt1 linear polymers may be conjugated to carrier. These linear polymers can comprise multiple copies of a single Rbt1 polypeptide, or combinations of different Rbt1 polypeptides, and can have tandem Rbt1 polypeptides, or Rbt1 polypeptides separated by other amino acid sequences. These linear polymers can be made using standard recombinant methods well known in the art. In another embodiment, Rbt1 multiple antigen peptides (Maps) are provided. Maps have a small immunologically inert core having radically branching lysine dendrites, onto which a number of Rbt1 polypeptides can be anchored (i.e., covalently attached). Posnett et al. (1988) J. Biol. Chem. 263:1719–1725; Tam (1989) Meth Enz. 168:7–15. The result is a large macromolecule having a high molar ratio of Rbt1 polypeptides to core. Maps are useful, efficient immunogens as well as usefull antigens for assays such as ELISA. Rbt1 Maps can be made synthetically and can be obtained commercially (Quality Controlled Biochemicals, Inc. Hopkinton, Mass.) In a typical Map system, a core matrix is made up of three levels of lysine and eight amino acids for anchoring Rbt1 polypeptides. The Map may be synthesized by any method known in the art, for example. a solid-phase method, for example, R. B. Merrifield (1963) *J.Am. Chem. Soc.* 85:2149.

In another embodiment, Rbt1 polypeptides can be conjugated with carrier or label. For example, in instances where the Rbt1 polypeptide is correctly configured so as to provide a binding site, but is too small to be immunogenic, the polypeptide may be linked to a suitable carrier. A number of techniques for obtaining such linkage are known in the art and need not be described in detail herein. Any carrier can be used which does not itself induce the production of antibodies harmful to the host. Suitable carriers are typically large, slowly metabolized macromolecules such as proteins; polysaccharides, such as latex functionalized sepharose, agarose, cellulose, cellulose beads and the like; polymeric amino acids, such as polyglutamic acid, polylysine, and the like; amino acid copolymers; and inactive virus particles or attenuated bacteria, such as Salmonella. Especially useful protein substrates are serum albumins, keyhole limpet hemacyanin, immunoglobulin molecules, thyroglobulin, ovalbumin, tetanus toxoid, and other proteins well known to those of skill in the art. Labels are known in the art and are described herein.

Compositions containing Rbt1 polypeptides are also encompassed by this invention. When these compositions are to be used pharmaceutically, they are combined with a pharmaceutically acceptable excipient.

Rbt1 polypeptides of the invention can be identified and/or characterized in a number of ways. For example, an Rbt1 polypeptide can be tested for its ability to bind to, for instance, another protein (such as an antibody). Alternatively, Rbt1 polypeptide(s) can be tested for its ability to elicit an immune response, whether humoral or cellular. It is understood that only one of these properties need be present in order for a polypeptide to come within this invention, although more than one of these properties may be present.

The ability of an Rbt1 polypeptide to bind (i.e., interact with) another protein can be assessed using standard techniques in the art. Binding of an Rbt1 polypeptide to an antibody may be assessed, for example, by RIA (i.e., by reacting radiolabeled Rbt1 polypeptide with an antibody that is coated on microtiter plates). In another procedure, binding to an antibody is determined by competitive immunoassay. For example, a fragment is tested for its ability to interfere with the binding between the antibody and another polypeptide known to bind to the antibody. This assay may be conducted by labeling one of the components (i.e., antibody or polypeptide known to bind to the antibody), and optionally immobilizing the other member of the binding pair on a solid support for ease of separation. The test fragment is incubated with labeled region, and then the mixture is presented to the immobilized target to determine if the test fragment is able to inhibit binding.

In the case of testing whether the Rbt1 polypeptide binds to another protein, for instance, a protein associated hyphal filaments of *C. albicans*, assays to detect binding are known in the art and need not be described in detail herein. For instance, a protein is immobilized on a suitable column. Extracts or solutions containing the test Rbt1 polypeptide are then run through the column, and a determination is made whether the Rbt1 polypeptide was retained on the column. Conversely, the Rbt1 polypeptides can be immobilized on a column and cell extracts or lysates are allowed to run through the column. Alternatively, the two hybrid technique can be used to identify polypeptides that interact with Rbt1 polypeptides (as well as, the cDNAs that encode such polypeptides) and to test such interactions. Brent et al. U.S. Pat. No. 5,580,736.

For characterizing an Rbt1 polypeptide for its ability to elicit an immune response (whether humoral or cellular) in an individual, standard assays exist in the art. For instance, the ability of an Rbt1 polypeptide to generate a humoral response can be determined by testing for the presence of an antibody that binds to the Rbt1 polypeptide(s) after administration of the Rbt1 polypeptide(s). It is understood that this antibody was not present, or was present in lower amounts, before administration of the Rbt1 polypeptide(s). Immunogenicity is preferably tested in individuals without a previous anti-Rbt1 response. Exanples of suitable individual include, but are not limited to, mice, rats, rabbits, goats, monkeys and humans. For this test, an individual is administered an Rbt1 polypeptide(s). The amount per administration and the number of administrations will vary, depending on the individual. Presence of an antibody elicited in response to administration of an Rbt1 polypeptide(s) is determined by standard assays in the art, such as ELISA or RIA. Rbt1 polypeptide(s) may be further characterized by their ability to elicit an antibody that is cytotoxic, or to elicit an antibody that participates in an ADCC response using standard assays in the art.

A Rbt1 polypeptide can also be characterized by its ability to elicit a cellular immune response, using, for example, assays that detect proliferation of peripheral blood mononuclear cells (PBMs) incubated with an Rbt1 polynucleotide. Another way of detecting a cellular immune response is to test for T cell cytotoxicity (CTL) activity. Both of these responses are detected using standard assays in the art.

Preparation of polypeptides of this invention

The polypeptides of this invention can be made by procedures known in the art. The polypeptides can be produced by recombinant methods (i.e., single or fusion polypeptides) or by chemical synthesis. Polypeptides, especially shorter polypeptides up to about 50 amino acids, are conveniently made by chemical synthesis. Methods of chemical synthesis are known in the art and are commercially available. For example, a polypeptide could be produced by an automated polypeptide synthesizer employing the solid phase method. Polypeptides can also be made by chemical synthesis using techniques known in the art.

Polypeptides can also be made by expression systems, using recombinant methods. The availability of polynucleotides encoding polypeptides permits the construction of expression vectors encoding intact (i.e., native) polypeptide, functionally equivalent fragments thereof, or recombinant forms. A polynucleotide encoding the desired polypeptide, whether in fused or mature form, and whether or not containing a signal sequence to permit secretion, may be ligated into expression vectors suitable for any convenient host. Both eukaryotic and prokaryotic host systems can be used. The polypeptide is then isolated from lysed cells or from the culture medium and purified to the extent needed for its intended use. Purification or isolation of the polypeptides expressed in host systems can be accomplished by any method known in the art. For example, cDNA encoding a polypeptide intact or a fragment thereof can be operatively linked to a suitable promoter, inserted into an expression vector, and transfected into a suitable host cell. The host cell is then cultured under conditions that allow transcription and translation to occur, and the desired polypeptide is recovered. Other controlling transcription or translation segments, such as signal sequences that direct the polypeptide to a specific cell compartment (i.e., for secretion), can also be used. Examples of prokaryotic host cells are known in the art and include, for example, E. coli and B. subtilis. Examples of eukaryotic host cells are known in the art and include yeast, avian, insect, plant, and animal cells such as COS7, HeLa, CHO and other mammalian cells.

When using an expression system to produce Rbt1 polypeptides, it is often preferable to construct a fusion protein that facilitates purification. Examples of components for these fusion proteins include, but are not limited to myc, HA, FLAG, His-6, glutathione S-transferase, maltose binding protein or the Fc portion of immunoglobulin. These methods are known in the art.

Alternatively, in vitro expression systems may also be used to produce Rbt1 polypeptides. A plasmid containing an RBT1 polynucleotide, under the control of an appropriate promoter, can be transcribed and the resultant RNA translated in vitro through the use of commercially available reagents. Such methods can be used to produce relatively pure, although small amounts of the polypeptide and are known in the art.

Preferably, especially if used for diagnostic purposes, the polypeptides are at least partially purified from other cellular constituents. Preferably, the polypeptides are at least 50% pure. In this context, purity is calculated as a weight percent of the total protein content of the preparation. More preferably, the proteins are 50–75% pure. More highly purified polypeptides may also be obtained and are encompassed by the present invention. For clinical use, the polypeptides are preferably highly purified, at least about 80% pure, and free of pyrogens and other contaminants. Methods of protein purification are known in the art and are not described in detail herein.

Uses of polypeptides

The polypeptides of this invention have a variety of uses. They can be used, for example, to detect the presence of an antibody that binds to Rbt1 polypeptide(s) or fragment(s) thereof. They may also be used to raise antibodies in a suitable host, which may be rabbits, mice, goats, or humans, as non-inclusive examples. It is possible that such antibodies, when present in humans, may confer some degree of protection or resistance against C. albicans pathogenesis, including initial infection and spread. It is also possible that these antibodies may provide a therapeutic function against C. albicans infection. The polypeptides of this invention thus may well prove to be useful in pharmaceutical applications, such as in therapeutic and/or prophylactic vaccines. Accordingly, the invention provides compositions comprising Rbt1 polypeptides. In some embodiments, these compositions further comprise a pharmaceutically acceptable excipient and are capable of eliciting an immune response in an individual when administered in an effective amount. In this context, an "effective amount" is an amount sufficient to elicit an immune response (whether humoral or cellular), and an effective amount may be administered in one or more administrations. Rbt1 polypeptides may also be used an agent to screen pharmaceutical candidates (both in vitro and in vivo), for rational (i.e., structure-based) drug design, as well as possible therapeutic uses as described above. Uses in pharmaceutical development will be described in more detail below.

Antibodies and their Preparation

Also provided by this invention are antibodies capable of specifically binding to Rbt1 polypeptide(s) of this invention.

The antibodies can be useful for, for example, diagnostic purposes, as described more fully below. These antibodies could be used to monitor TUP1 function in C. albicans as expression of Rbt1 is regulated by TUP1 activity. Antibodies of this invention can also be used for purification and/or isolation of Rbt1 polypeptides described herein.

In one embodiment, the invention provides a purified antibody capable of specifically binding to a polypeptide of this invention. As noted in the definition of "antibody" above, this includes fragments of antibodies, such as Fab fragments. In another embodiment, a monoclonal antibody is provided that is capable of specifically binding to a polypeptide of this invention.

Laboratory methods for producing polyclonal antibodies and monoclonal antibodies, as well as deducing their corresponding nucleic acid sequences, are known in the art. For example, see Harlow and Lane, *Antibodies: A Laboratory Manual*, Cold Spring Harbor Laboratory, New York (1988) and Sambrook et al. (1989).

The antibodies of this invention may be polyclonal or monoclonal. Polyclonal antibodies of this invention can be biologically produced by introducing a polypeptide (or fragment of a polypeptide) of this invention into an animal, e.g., rabbit. Monoclonal antibodies of this invention can be biologically produced by introducing a polypeptide (or fragment of a polypeptide) of this invention into an animal, e.g., mouse or rat. The antibody producing cells in the animal are isolated and fused with myeloma cells or heteromyeloma cells to produce hybrid cells or hybridomas. Accordingly, the invention also includes a monoclonal Ab capable of specifically binding to an Rbt1 polypeptide. The invention also includes hybridoma cells producing the monoclonal antibodies of this invention.

Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) *Proc. Natl. Acad. Sci.* 82:8653 or Spira et al. (1984) *J. Immunol. Methods* 74:307.

Thus, using Rbt1 polypeptide(s) of this invention or fragment(s) thereof, and well known methods, one of skill in the art can produce and screen the hybridoma cells and antibodies of this invention for antibodies having the ability to bind polypeptide(s) of this invention.

If a monoclonal antibody being tested binds with Rbt1 polypeptide(s) of this invention, then the antibody being tested and the antibodies provided by the hybridomas of this invention are equivalent. It also is possible to determine without undue experimentation whether an antibody has the same specificity as a monoclonal antibody of this invention by determining whether the antibody being tested prevents a monoclonal antibody of this invention from binding the polypeptide(s) with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with the polypeptide(s) with which it is normally reactive, and determine if the monoclonal antibody being tested is inhibited in its ability to bind the antigen. If the monoclonal antibody being tested is inhibited, then, in all likelihood, it has the same, or a closely related, epitopic specificity as the monoclonal antibody of this invention.

As noted above, this invention also provides biological active fragments of the polyclonal and monoclonal antibodies described above. These antibody fragments retain some ability to selectively bind with its antigen or immunogen. Examples of antibody fragments are known in the art and include, but are not limited to, CDR regions, Fab, Fab', $F(ab')_2$, $F_v$, and single chain methods. Methods of making these fragments are known in the art, see for example, Harlow and Lane, (1988).

The antibodies of this invention also can be modified to create chimeric antibodies and humanized antibodies (Oi et al. (1986) *BioTechniques* 4(3):214). Chimeric antibodies are those in which the various domains of the antibodies' heavy and light chains are coded for by DNA from more than one species.

The isolation of other hybridomas secreting monoclonal antibodies with the specificity of the monoclonal antibodies of the invention can also be accomplished by one skilled in the art by producing anti-idiotypic antibodies (Herlyn, et al. (1986) *Science* 232: 100). An anti-idiotypic antibody is an antibody which recognizes unique determinants present on the monoclonal antibody produced by the hybridoma of interest. These determinants are located in the hypervariable region of the antibody. It is this region which binds to a given epitope and, thus, it is responsible for the specificity of the antibody. The anti-idiotypic antibody can be prepared by immunizing an animal with the monoclonal antibody of interest. The animal immunized will recognize and respond to the idiotypic determinants of the immunizing antibody by producing an antibody to these idiotypic determinants. By using the anti-idiotypic antibodies of the second animal, which are specific for the monoclonal antibodies produced by a single hybridoma which was used to immunize the second animal, it is now possible to identify other clones with similar idiotypes as the antibody of the hybridoma used for immunization.

Idiotypic identity between monoclonal antibodies of two hybridomas demonstrates that the two monoclonal antibodies are the same with respect to their recognition of the same epitopic determinant. Thus, by using antibodies to the epitopic determinants on a monoclonal antibody it is possible to identify other hybridomas expressing monoclonal antibodies of the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the mirror image of the epitope bound by the first monoclonal antibody. Thus, in this instance, the anti-idiotypic monoclonal antibody could be used for immunization for production of these antibodies.

The antibodies of this invention can be linked (i.e., conjugated) to a detectable agent or a hapten. The complex is usefull to detect the polypeptide(s) (or polypeptide fragment(s)) to which the antibody specifically binds in a sample, using standard immunochemical techniques such as immunohistochemistry as described by Harlow and Lane (1988). Examples of types of immunoassays which can utilize monoclonal antibodies of the invention are competitive and non-competitive immunoassays in either a direct or indirect format. Examples of such immunoassays are the enzyme linked immunoassay (ELISA), radioimmunoassay (RIA), and the sandwich (immunometric) assay. Detection of using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Another technique which may also result in greater sensitivity consists of coupling the antibodies to low molecular weight haptens. These haptens can then be specifically detected by means of a second reaction. For example, it is common to use such haptens as biotin, which reacts avidin, or dinitropherryl, pyridoxal, and fluorescein, which can react with specific anti-hapten antibodies. See Harlow and Lane (1988).

The monoclonal antibodies of the invention can be bound to many different carriers. Thus, this invention also provides compositions containing antibodies and a carrier. Carriers can be active and/or inert. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

The monoclonal antibodies of this invention may further comprise a label. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

For purposes of the invention, polypeptides of this invention may be detected by the monoclonal antibodies of the invention when present in biological fluids and tissues. This use of antibodies is discussed in more detail below.

Compositions containing the antibodies, fragments thereof or cell lines which produce the antibodies, are encompassed by this invention. When these compositions are to be used pharmaceutically, they are combined with a pharmaceutically acceptable carrier.

Use of RBT1 Polynuleofides, Polypeptides, and Antibodies in Diagnosis and/or Clinical Management Presently, diagnostic methods for *C. albicans* are cumbersome, requiring culturing and microscopic examination for germ tube formation. See, for example, Warren et al. (1991) *Manual of Clin. Micro* (5th ed.) at 617–629. RBT1 polynucleotides, polypeptides encoded by these sequences, and antibodies specific for these polypeptides, are potentially useful as diagnostic and/or clinical management aids. More specifically, detection of these polynucleotide and/or polypeptide sequences in cells, body fluids or other biological samples can help identify those cells as being infected by *C. albicans* and thereby play a part in the initial diagnosis. As the presence of RBT1 mRNA and/or polypeptide sequences are indicative of TUP1 function and/or filamentous growth, they may also indicate, for example, the degree of virulence and/or particular antibiotic resistance or susceptibility, and thus provide information regarding prognosis as well as appropriate treatment options. These detection procedures may be performed by diagnostic laboratories, experimental laboratories, clinical practitioners, or private individuals. Generally, to perform a diagnostic method of this invention, one of the compositions of this invention is provided as a reagent to detect a target with which it reacts in a biological sample. The target is supplied by obtaining a suitable biological sample from an individual for whom the diagnostic parameter is to be measured. Many types of samples are suitable for this purpose, including those that are obtained at or near the suspected site of infection. If desired, the target may be partially purified from the sample or amplified before the assay is conducted.

For patients already diagnosed with C. albicans infection, detection of these sequences may assist with clinical management. For example, presence of a sequence particularly associated with an aspect of infection, such as aggressiveness or antibiotic resistance, may be a usefull predictor of susceptibility to various regimens of standard therapy, the extent of disease, and/or its aggressiveness. Any or all of these determinations can be important in helping a clinician choose and adjust available treatment options.

The polynucleotide(s), polypeptide(s), and antibodies embodied in this invention provide specific reagents that can be used in standard diagnostic procedures (i.e., clinical detection methods). The actual procedures for conducting diagnostic tests are extensively known in the art, and are routine for a practitioner of ordinary skill. See, for example, U.S. Pat. No. 4,968,603 (Slamon et al.), and PCT Applications WO 94/00601 (Levine et al.) and WO 94/17414 (K. Keyomarsi et al.). What follows is a brief non-limiting survey of some of the known procedures that can be applied.

Generally, to perform a diagnostic method of this invention, a composition(s) of this invention is provided as a reagent to detect a target with which it reacts in a clinical sample. Thus, a polynucleotide of this invention can be used as a reagent to detect a DNA or RNA target, that might be present in a cell infected by C. albicans. A polypeptide of this invention can be used as a reagent to detect a target for which it has a specific binding site, such as an antibody molecule or (if the polypeptide is a receptor or enzyme) the corresponding ligand. An antibody can be used as a reagent to detect a target it specifically recognizes, such as the polypeptide used as an immunogen to raise it.

The target is supplied by obtaining a suitable biological sample from an individual for whom the diagnostic and/or clinical management parameter is to be measured. Relevant clinical samples are those obtained from individuals suspected of having (or known to have, in the case of clinical management) C. albicans infection. Many types of samples are suitable for this purpose, including those that are obtained at or near the suspected primary infection site by biopsy, in vitro cultures of cells derived therefrom, blood, and blood components. If desired, the target may be partially purified from the sample or amplified before the assay is conducted. Methods for purifying polynucleotides and proteins from biological sources are known in the art.

The reaction between reagent and target is performed by contacting a reagent with a sample under conditions that will allow a complex to form between the reagent and the target. The reaction may be performed in solution, or on a solid tissue sample, for example, using histology sections, or on an inert matrix, such as coated beads. The complex (if present) is detected by a number of techniques known in the art. For example, the reagent may be supplied with a label and unreacted reagent may be removed from the complex, the amount of remaining label thereby indicating the amount of complex formed. Further details regarding complex formation and detection are provided in the descriptions that follow.

Polynucleotides

RBT1 polynucleotides can be used as hybridization probes for detection of, for example, the presence of RBT1 polynucleotides in a cell. For instance, an RBT1 polynucleotide could be used as a probe to determine the presence of C. albicans polynucleotide sequences in cells suspected of being infected by C. albicans. Accordingly, the invention provides methods for detecting a polynucleotide from C. albicans in a biological sample comprising the steps of (a) contacting the polynucleotide from C. albicans from the sample with a polynucleotide of this invention under conditions that permit the formation of a stable duplex and (b) detecting the stable duplex formed in step (a), if any. In another embodiment, the invention provides methods for detecting a polynucleotide from C. albicans in a biological sample comprising the steps of (a) conducting an amplification reaction on a polynucleotide in the sample using a primer consisting of a fragment of the polynucleotide sequence of SEQ ID NO:1 and (b) detecting the presence of amplified copies of the polynucleotide, if any. Alternatively, the primer may consist of a fragment of the polynucleotide sequence of SEQ ID NO:3.

For these methods, a suitable cell sample or a sample derived from cells (either of which are suspected of containing RBT1 polynucleotide sequences) is obtained and tested for the presence of RBT1 polynucleotide by contacting the polynucleotides from the sample with the RBT1 polynucleotide probe. The method is conducted to allow hybridization to occur between the RBT1 probe and RBT1 polynucleotide of interest, and the resultant (if any) hybridized complex is detected. Such methods entail procedures well known in the art, such as cell culture, polynucleotide preparation, hybridization, and detection of hybrid complexes formed, if any. Using similar methods, the probes can also be used to detect vectors which are in turn used to produce Rbt1 polypeptides, intact Rbt1, or recombinant, variant forms of Rbt1.

The reaction is performed by contacting an RBT1 polynucleotide under conditions that will allow a stable complex to form between the RBT1 polynucleotide and a polynucleotide target. Complex formation is detected by a number of techniques known in the art. The assay result is preferably compared with a similar assay conducted on a control sample, preferably a sample from an uninfected source (negative control). It is often preferable to conduct the assay on the test sample and control sample simultaneously.

These diagnostic assays may be rendered specific by, for example (a) performing a hybridization reaction with a specific probe; (b) performing an amplification with a specific primer; or (c) combination of (a) and (b). To perform an assay that is specific due to hybridization with a specific probe, a polynucleotide is chosen with the required degree of complementarity for the intended target polynucleotide. Preferred probes include polynucleotides of at least about 15 nucleotides in length. Increasingly preferred are probes comprising at least about 20, 25, 30, 50 or 100 polynucleotides.

The probe may be provided with a label. Some of the labels often used include radioisotopes such as $^{32}P$ and $^{33}P$, chemiluminescent or fluorescent reagents such as fluorescein, and enzymes such as alkaline phosphatase that are capable of producing a colored solute or precipitant. The label may be intrinsic to the reagent, it may be attached by direct chemical linkage, or it may be connected through a series of intermediate reactive molecules, such as a biotin-avidin complex, or a series of inter-reactive polynucleotides. The label may be added to the reagent before hybridization with the target polynucleotide, or afterwards. To improve the sensitivity of the assay, it is often desirable to increase the signal ensuing from hybridization. This can be accomplished by using a combination of serially hybridizing polynucleotides or branched polynucleotides in such a way that multiple label components become incorporated into each complex. See U.S. Pat. No. 5,124,426.

If desired, the target polynucleotide may be extracted from the sample, and may also be partially purified. The target polynucleotide may be optionally subjected to any combination of additional treatments, including digestion with restriction endonucleases, size separation (by electrophoresis in agarose or polyacrylamide, for example), and affixation to a reaction matrix, such as a blotting material.

Hybridization is allowed to occur by mixing the RBT1 polynucleotide with a sample suspected of containing target polynucleotide under appropriate reaction conditions. This may be followed by washing or separation to remove unreacted reagent. Generally, both target polynucleotide and RBT1 polynucleotide are at least partly equilibrated into the single-stranded form (i.e., denatured) in order for complementary sequences to hybridize efficiently.

The level of hybridization stringency depends, inter alia, upon the objective of the test and the particular RBT1 polynucleotide used. For example, a preferred set of conditions for use with a preferred probe of 50 nucleotides or more is 6×SSC at 37° C. in 50% formarnide, followed by a wash at low ionic strength. This will generally require that the polynucleotide target be at least about 90% identical with the RBT1 polynucleotide for a stable duplex to form. The specificity of the reaction may also be increased by increasing the length of the RBT1 polynucleotide used.

Appropriate hybridization conditions are determined to permit hybridization of the probe only to *C. albicans* sequences. Conditions may be estimated beforehand using the formula given above. Preferably, the exact conditions are confirmed by testing the RBT1 polynucleotide with separate samples known to contain target *C. albicans* polynucleotides as well as polynucleotides that are not desired to be detected. Such samples may be provided either by synthesizing the polynucleotides from published sequences, or by extracting and amplifying DNA from tissues known to be infected with *C. albicans*. Preferably, probes share little to no sequence homology with human sequences. However, even if there are shared sequences, such a probe may still be usefull if detection systems allow discrimination between signal due to hybridization to *C. albicans* sequences and signal due to hybridization to human sequences. If it is additionally desirable to distinguish between and/or among various Candida species, the probe (due to length and/or sequence content) and/or hybridization conditions should be adjusted and selected such that these sequences may be distinguished.

Another method of detecting polynucleotide target is by using PCR. All processes of producing replicate copies of the same polynucleotide, such as PCR or gene cloning, are collectively referred to herein as "replication". PCR primers consisting of sequences unique to RBT1 may be used to amplify any such sequences in the sample. Preferably, a sample known not to contain any *C. albicans* sequences is used as a negative control. PCR methods are well known in the art and need not be described herein. For these methods, DNA or RNA is prepared from a sample. Optionally, target polynucleotide is pre-amplified by PCR using primers which are specific to Candida, preferably *C. albicans*. The target is then amplified using RBT1-specific primers. Preferably, two rounds of amplification are performed using oligonucleotide primers in a nested fashion, i.e., non-specific in the first round followed by *C. albicans* in the second round. This provides an assay which is both sensitive and specific.

The primers used consist of fragments of SEQ ID NO:3 or SEQ ID NO:1. Preferably, at least one, preferably both, of the primers are sequences unique to *C. albicans*. Alternatively, if the expected size of the amplified *C. albicans* reaction product is known and different from that of the non-target (for example, host) polynucleotides, the sequences of the primers need not be unique. Generally, the primer is about 15 to 20 nucleotides in length, although longer primer of 30 to 50 nucleotides may be used.

A positive test may be indicated by the presence of sufficient reaction product at the end of the amplification series. Amplified polynucleotide may be detected on an agarose gel upon staining with ethidium bromide. Alternatively, a radiolabeled substrate may be added to the mixture during the final amplification cycle. The incorporated label may be separated from unincorporated label (e.g., by blotting or by size separation) and the label may be detected by, for example, counting or autoradiography. If run on an agarose or polyacrylamide gel, the size of the product may help confirm the identify of the amplified fragment. Specific amplification may also be followed by specific hybridization, by using the amplification mixture obtained from the foregoing procedure as a target source for the hybridization reaction outlined above.

Polypeptides

A polypeptide embodied in this invention can also be used as a reagent for determining *C. albicans* that may be present via the detection of antibodies that specifically bind to Rbt1 polypeptides of this invention. For example, *C. albicans* DNA and/or RNA in affected cells may result in the corresponding polypeptide(s) being produced by the cells. This in turn may result in stimulation of the immune response of the host to produce its own antibody molecules that are specific for the polypeptide(s).

Accordingly, the invention includes methods for detecting an anti-*Candida albicans* antibody in a biological samples, in which the steps are (a) contacting antibody from the sample with an Rbt1 polypeptide (i.e., a polypeptide of this invention) under conditions which permit formation of a stable antigen-antibody complex, and (b) detecting stable complex formed, if any.

To use the polypeptide(s) of this invention in the detection of such antibodies in an individual suspected of having *C. albicans* infection, an immunoassay is conducted. The polypeptide(s) is provided as a reagent, and the antibody is the target in the biological sample. For example, human IgG antibody molecules present in a serum sample may be captured with solid-phase protein A, and then overlaid with the labeled polypeptide reagent. The amount of antibody would then be proportional to the label attached to the solid phase. Alternatively, cells or tissue sections expressing the polypeptide may be overlaid first with the test sample containing the antibody, and then with a detecting reagent such as labeled anti-immunoglobulin. The amount of antibody would then be proportional to the label attached to the cells. The amount of antibody detected in the sample would be compared with the amount detected in a control sample.

Antibodies

An antibody embodied in this invention can also be used as a reagent in diagnosis and/or clinical management to detect Rbt1 polypeptide(s) from *C. albicans*. Accordingly, the invention includes methods for detecting a *C. albicans*

Rbt1 polypeptide (i.e., a polypeptide of this invention) in a biological sample, in which the steps are: (a) contacting polypeptide from the sample with an anti-Rbt1 antibody described herein under conditions that permit the formation of a stable antigen-antibody complex and (b) detecting stable complexes formed, if any. Any such polypeptide can be detected in biological samples by immunochemical and/or immunohistological techniques that will be apparent to a practitioner of ordinary skill.

The antibody used as a reagent may be provided directly with a suitable label. More frequently, the antibody is detected using one of a number of developing reagents which are easily produced or available commercially. Typically, these developing reagents are anti-immunoglobulin or protein A, and they typically bear labels which include, but are not limited to, fluorescent markers such as fluorescein, enzymes such as peroxidase that are capable of precipitating a suitable chemical compound or that emit light by way of a chemical reaction, electron dense markers such as colloidal gold, or radioisotopes such as $^{125}$I, $^{35}$S, or $^{32}$P.

The amount of polypeptide may be detected in a standard quantitative immunoassay. If the protein is secreted or shed from the cell in any appreciable amount, or is present in white blood cells, it may be detectable in plasma or serum samples. Alternatively, the target protein may be solubilized or extracted from a solid tissue sample. Before quantitating, the protein may optionally be affixed to a solid phase, such as by a blot technique or using a capture antibody.

A number of immunoassay methods are established in the art for performing the quantitation. For example, the protein may be mixed with a pre-determined non-limiting amount of the reagent antibody specific for the protein. The reagent antibody may contain a directly attached label, such as an enzyme or a radioisotope, or a second labeled reagent may be added, such as anti-immunoglobulin or protein A. For a solid-phase assay, unreacted reagents are removed by washing. For a liquid-phase assay, unreacted reagents are removed by some other separation technique, such as filtration or chromatography. The amount of label captured in the complex is positively related to the amount of target protein present in the test sample. A variation of this technique is a competitive assay, in which the target protein competes with a labeled analog for binding sites on the specific antibody. In this case, the amount of label captured is negatively related to the amount of target protein present in a test sample. Results obtained using any such assay on a sample from a suspected infected source are compared with those from a non-infected source.

Kits Conmrising RBT1 Polynucleotides, Polypeptides and/or Antibodies

This invention also encompasses kits containing RBT1 polynucleotide(s), polypeptide(s), and/or antibodies described herein, preferably diagnostic kits. For example, the presence of C. albicans DNA can be tested using the polynucleotides of this invention. As another example, the presence of C. albicans Rbt1 protein products could be detected using an antibody of this invention (or a polypeptide that binds to the protein product). A clinical sample is optionally pre-treated for enrichment of the target being tested for. A reagent contained in the kit is then applied in order to detect the diagnostic component. Kits embodied by this invention include those that allow someone to conduct an assay for C. albicans presence and/or activity, such as any of those disclosed herein, thus detecting and/or quantitating the extent of the presence and/or those activities.

Diagnostic procedures using RBT1 polynucleotides, polypeptides, and/or antibodies of this invention can be performed by diagnostic laboratories, experimental laboratories, practitioners, or private individuals. Kits embodied by this invention include those that allow someone to conduct an assay for the presence of RBT1 sequences, Rbt1 polypeptides, and/or anti-Rbt1 antibodies, such as any of those disclosed herein, thus detecting and/or quantitating those activities. The kits embodied by this invention also include kits that allow detection of RBT1 polynucleotides in, for example, ex vivo or in vivo transfected cells. These kits can be used for detection or quantitation of a polynucleotide that comprises a polynucleotide encoding an RBT1 or a portion thereof. Accordingly, the invention includes (a) a kit for detection or quantification of a polynucleotide comprising a C. albicans RBT1 polynucleotide or a fragment thereof (including RBT1 polynucleotides encoding C. albicans Rbt1 or a fragment thereof) in a biological sample; (b) a kit containing anti-Rbt1 antibodies for detection or quantification of a C. albicans polypeptide in a biological sample; (c) a kit containing Rbt1 polypeptide for detection or quantification of an anti-C. albicans antibody in a biological sample.

Each kit comprises the reagent which renders the procedure specific: an RBT1 polynucleotide, used for detecting target DNA or RNA; an Rbt1 polypeptide, used for detecting target antibody that may be present in a sample to be analyzed, or an anti-Rbt1 antibody, used for detecting target protein. The reagent is supplied in a solid form or liquid buffer that is suitable for storage, and later for exchange or addition into the reaction medium when the test is performed. The kit may optionally provide additional components that are useful in the procedure. These optional components include, but are not limited to, buffers, capture reagents, developing reagents, labels, reacting surfaces, means for detection, control samples, instructions, and interpretive information. Suitable packaging is provided.

Use in Pharmceutical Development: Screening

The invention also encompasses methods of screening pharmaceutical candidates using the RBT1 polynucleotide(s), polypeptide(s), and/or antibodies of this invention. As mentioned above, TUP1 function has been shown to play an important role in filament formation and tup1 mutant C. albicans is poorly infective in mice. Because RBT1 sequences are associated with C. albicans TUP1 function and with filamentous growth, modulating the expression of the RBT1 gene or the activity of the Rbt1 polypeptide may modify the infection/virulence process and thus play an important role in therapy, prophylaxis, or both.

The invention includes a method for identifying an agent that may control virulence in C. albicans, comprising: (a) contacting at least one agent to be tested with a C. albicans cell that has RBT1 function and (b) analyzing at least one characteristic which is associated with a modulation of RBT1 function in said host cell, wherein an agent is identified by its ability to elicit at least one such characteristic. In another embodiment, the invention includes a composition for controlling virulence in C. albicans comprising an agent thus identified.

The invention includes a method of inhibiting virulence of C. albicans comprising modulating C. albicans RBT1 function. In one embodiment, modulation of RBT1 function is achieved by disrupting at least one RBT1 gene of C. albicans.

Thus, this invention includes methods of screening agents using polynucleotide(s), polypeptide(s) and/or anti-Rbt1 antibodies described herein. The general screening strategy is to introduce a pharmaceutical candidate and then determine whether the effect (if any) is beneficial, and preferably specific. Application of the agent can be direct (such as determining whether a candidate binds to the polypeptide or polynucleotide in the assay) in an in vitro system, but also be used in an in vivo system, such as cell culture. For example, an agent that modulates the activity of a polynucleotide or polypeptide described herein has the potential to block any associated pathology when administered. It is not necessary that the mechanism of modulation be known; only that the alteration affect infected cells preferably without being significantly detrimental to other, uninfected cells.

Another embodiment of this invention includes a method of inhibiting virulence of C. albicans comprising modulating C. albicans RBT1 function, wherein RBT1 function is modulated by contact with an agent thus identified.

Modulation of RBT1 finction may occur at any level that affects RBT1 function. An agent may modulate RBT1 finction by preventing, reducing or increasing transcription of RBT1. An example of such an agent is one that binds to the upstream controlling region, including a polynucleotide sequence or polypeptide. An agent may modulate RBT1 function by preventing, reducing or increasing translation of RBT1 mRNA. An example of such an agent is one that binds to the mRNA, such as an anti-sense polynucleotide, or an agent which selectively degrades the mRNA, or an agent that selectively stabilizes the mRNA. An agent may modulate RBT1 function by binding to an Rbt1 polypeptide. An example of such an agent is a polypeptide or a chelator. Examples of the affect of such Rbt1-binding agents may include the degradation of the Rbt1 polypeptide, the increased half-life of the Rbt1 polypeptide, the prevention of Rbt1 interaction with a ligand, and the stabilization of Rbt1 with a ligand.

The agent can be any compound, complex or substance. Generally, the choice of agents to be screened is governed by several parameters, such as the particular polynucleotide or polypeptide target, its perceived finction, its three-dimensional structure (if known or surmised), and other aspects of rational drug design. Techniques of combinatorial chemistry can also be used to generate numerous permutations of candidates. Those of skill in the art can devise and/or obtain suitable agents for testing.

In vitro screening methods

In in vitro screening methods of this invention, an agent is screened in an in vitro system, which may include either of the following: (1) an assay for an agent which modulates the translation of RBT1 mRNA or a polynucleotide encoding Rbt1 polypeptide; (2) an assay for an agent that binds to C. albicans RBT1 polynucleotides or Rbt1 polypeptide.

For an assay that determines whether an agent modulates the translation of RBT1 mRNA or a polynucleotide encoding Rbt1, an in vitro transcription/translation system may be used. These systems are available commercially and provide an in vitro means to produce mRNA corresponding to a polynucleotide sequence of interest. After RBT1 mRNA is made, it can be translated in vitro and the translation products compared. Comparison of translation products between an in vitro expression system that does not contain any agent (negative control) with an in vitro expression system that does contain an agent indicates whether the agent is affecting RBT1 translation. Comparison of translation products between control and RBT1 polynucleotides indicates whether the agent, if acting on this level, is selectively affecting translation of RBT1 (as opposed to affecting translation in a general, non-selective or non-specific fashion).

In an example for an assay for an agent that binds to a C. albicans polypeptide, RBT1 is first recombinantly expressed in a prokaryotic or eukaryotic expression system as a native or as a fusion protein in which the Rbt1 polypeptide is conjugated with a well-characterized epitope or protein as described above under "Preparation of polypeptides of this invention". Recombinant Rbt1 is then purified by, for instance, immunoprecipitation using anti-Rbt1 antibodies or anti-epitope antibodies or by binding to immobilized ligand of the conjugate. An affinity column made of Rbt1 or Rbt1-fusion protein is then used to screen a mixture of compounds which have been appropriately labeled. Suitable labels include, but are not limited to fluorochromes, radioisotopes, enzymes and chemiluminescent compounds. The unbound and bound compounds can be separated by washes using various conditions (e.g. high salt, detergent) that are routinely employed by those skilled in the art. Non-specific binding to the affinity column can be minimized by pre-clearing the compound mixture using an affinity column containing merely the conjugate or the epitope. Similar methods can be used for screening for an agent(s) that competes for binding to Rbt1 polypeptides. In addition to affinity chromatography, there are other techniques such as measuring the change of melting temperature or the fluorescence anisotropy of a protein which will change upon binding another molecule. For example, a BIAcore assay using a sensor chip (supplied by Pharmacia Biosensor, Stitt et al. (1995) *Cell* 80: 661–670) that is covalently coupled to native Rbt1, Rbt1 fragments, or Rbt1-fusion proteins, may be performed to determine the Rbt1 binding activity of different agents.

It is also understood that the in vitro screening methods of this invention include structural, or rational, drug design, in which the amino acid sequence, three-dimensional atomic structure or other property (or properties) of an Rbt1 polypeptide provides a basis for designing an agent which is expected to bind to an Rbt1 polypeptide. Generally, the design and/or choice of agents in this context is governed by several parameters, such as the perceived function of the Rbt1 polypeptide target, its three-dimensional structure (if known or surmised), and other aspects of rational drug design. Techniques of combinatorial chemistry can also be used to generate numerous permutations of candidate agents. For purposes of this invention, an agent designed and/or obtained by rational drug designed may also be tested on C. albicans growth in cell culture and/or infectivity in animal models.

It is also understood that anti-Rbt1 antibodies described herein can be used to determine whether agents which interact with Rbt1 polypeptides alter the structure and/or conformation of the Rbt1 polypeptide. For example, a conformational change and/or structural alteration induced by contact with an agent may result in the Rbt1 polypeptide becoming unrecognizable by the Rbt1-specific antibodies. The loss of the ability of a monoclonal anti-Rbt1 antibody to immunoprecipitate an Rbt1 polypeptide after the polypeptide has been contacted by the agent would suggest that the agent had interfered, either directly or through a conformational change and/or a structural alteration, with the antibody recognition site on the Rbt1 polypeptide. Other ways to assess this interaction are well known in the art. As such a change may alter Rbt1 function, agents screened for their effect on Rbt1- anti-Rbt1 interactions would be useful for the refinement of those agents known to interact with Rbt1 to those that may alter Rbt1 function.

In vivo screening methods

In in vivo screening assays, a living cell containing an expressed RBT1 gene, or RBT1 gene fragment, that is functionally equivalent to (i.e., is complemented by) *C. albicans* RBT1, or a living cell containing a polynucleotide construct comprising a *C. albicans* Rbt1 encoding sequence, or an Rbt1 fiagment encoding sequence, are exposed to an agent. In contrast (as described above), conventional drug screening assays have typically measured the effect of a test agent on an isolated component, such as an enzyme or other functional protein.

The in vivo screening assays described herein have several advantages over conventional drug screening assays: 1) if an agent must enter a cell to achieve a desired therapeutic effect, an in vivo assay can give an indication as to whether the agent can enter a cell; 2) an in vivo screening assay can identify agents that, in the state in which they are added to the assay system are ineffective to elicit at least one characteristic which is associated with modulation of *C. albicans* RBT1 function, but that are modified by cellular components once inside a cell in such a way that they become effective agents; 3) most importantly, an in vivo assay system allows identification of agents affecting any component of a pathway that ultimately results in characteristics that are associated with RBT1 function.

In general, screening is performed by adding an agent to a sample of appropriate cells, and monitoring the effect. The experiment preferably includes a control sample which does not receive the candidate. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, and the ability of the cells to interact with other cells or compounds. Differences between treated and untreated cells indicate effects attributable to the candidate. Optimally, the drug has a greater effect on experimental cells than on control cells.

In one embodiment, an agent is identified by its ability to elicit a characteristic associated with modulation of endogenous, host cell RBT1 finction in a suitable host cell.

To test for agents that upregulate the expression of RBT1, an example of a suitable host cell would be *C. albicans* grown in conditions in which RBT1 is repressed, e.g., when cells are in the budding yeast cell morphology. Under such conditions, an agent would be tested for its ability to result in increased expression of RBT1 mRNA and/or Rbt1 polypeptide.

To identify agents that specifically activate RBT1 gene transcription, the transcription regulatory regions of ihe RBT1 gene could be linked to a reporter gene and the construct added to an appropriate host cell. As used herein, the term "reporter gene" means a gene that encodes a gene product that can be identified (i.e., a reporter protein). Reporter genes include, but are not limited to, alkaline phosphatase, chloramphenicol acetyltransferase, P-galactosidase, luciferase and green fluorescence protein (GFP). Identification methods for the products of reporter genes include, but are not limited to, enzymatic assays and fluorimetric assays. Reporter genes and assays to detect their products are well known in the art and are described, for example in Ausubel et al. (1987) and periodic updates. Reporter genes, reporter gene assays and reagent kits are also readily available from commercial sources. Examples of appropriate cells include, but are not limited to, *C. albicans*, fungal, yeast, mammalian, and other eukaryotic cells. A practitioner of ordinary skill will be well acquainted with techniques for transfecting eukaryotic cells, including the preparation of a suitable vector, such as a viral vector; conveying the vector into the cell, such as by electroporation; and selecting cells that have been transformed, such as by using a reporter or drug sensitivity element. The effect of an agent on transcription from the RBT1 regulatory region in these constructs would be assessed through the activity of the reporter gene product.

The modulation of Rbt1 function can be accomplished in many ways including, but not limited to, those listed here. Besides the increase in expression under conditions in which it is normally repressed mentioned above, RBT1 expression could be decreased when it would normally be expressed. An agent could accomplish this through a decrease in transcription rate and the reporter gene system described above would be a means to assay for this. The host cells to assess such agents would be need to be permissible for RBT1 expression.

Cells transcribing RBT1 mRNA could be used to identify agents that specifically modulate the half-life of RBT1 mRNA and/or the translation of RBT1 mRNA. Such cells would also be used to assess the effect of an agent on the processing and/or post-translational modification of the Rbt1 polypeptide. An agent could modulate the amount of Rbt1 in a cell by modifying the turn-over (i.e., increase or decrease the half-life) of the Rbt1 polypeptides. The specificity of the agent with regard to the RBT1 mRNA and polypeptide would be determined by examining the RBT1 products in the absence of the agent and by examining the products of unrelated mRNAs and polypeptides. Methods to examine mRNA half-life, protein processing, and protein turn-over are well know to those skilled in the art.

In vivo screening methods could also be useful in the identification of agents that modulate Rbt1 function through the interaction with Rbt1 directly. Such agents could block normal Rbt1-ligand interactions, if any, or could enhance or stabilize such interactions. The effect of the agent could be determined using immunoprecipitation reactions. Anti-Rbt1 antibodies would be used to precipitate Rbt1 and any protein tightly associated with it. By comparing the polypeptides immunoprecipitated from treated cells and from untreated cells, an agent could be identified that would augment or inhibit Rbt1-ligand interactions, if any. Rbt1-ligand interactions could also be assessed using cross-linking reagents that convert a close, but noncovalent interaction between polypeptides into a covalent interaction. Techniques to examine protein-protein interactions are well known to those skilled in the art.

In another embodiment, the invention provides a method for identifying an agent that may control virulence in *C. albicans*, said method comprising: (a) introducing a polynucleotide encoding *C. albicans* Rbt1 or a finctional fragment thereof into a suitable host cell that otherwise lacks RBT1 function, wherein RBT1 function is restored in said host cell; (b) contacting said host cell of step (a) with at least one agent to be tested; (c) analyze at least one characteristic which is associated with a modulation of RBT1 function in said host cell, wherein an agent is identified by its ability to elicit at least one such characteristic.

As described in Examples 1 and 2, the RBT1 gene is expressed in *C. albicans* cells lacking TUP1 function and in wild type cells induced to a filamentous morphology by the presence of serum in the growth medium. Cells expressing RBT1 (i.e., cells without TUP1 function or grown in such conditions as to permit RBT1 expression) would be appropriate host cells to assess the ability of an agent to modulate Rbt1 function. Alternatively, should RBT1 expression in *S. cerevisiae* induce a phenotype similar to that of its expression in *C. albicans* (e.g., filamentous growth), such *S.* cerevisiae expressing *C. albicans* RBT1 would also be suitable host cells to screen for agents that affect Rbt1 function. Methods of using and manipulating *S. cerevisiae* are well-known in the art.

The screening methods described above represent primary screens, designed to detect any agent that may exhibit anti-fingal activity. The skilled artisan will recognize that secondary tests will likely be necessary in order to evaluate an agent irther. For example, a secondary screen may comprise testing the agent(s) in *C. albicans* if the initial screen has been performed in a host cell other than *C. albicans*. A further screen is to perform an infectivity assay using the cells that have been treated with the agent(s). An infectivity assay using mice and other animal models (such as rat) are known in the art. In addition, a cytotoxicity assay would be performed as a further corroboration that an agent which tested positive in a primary screen would be suitable for use in living organisms. Any assay for cytotoxicity would be suitable for this purpose, including, for example the MTT assay (Promega).

*Candida albicans* Cells having Compromised RBT1 Function

The invention also provides isolated *C. albicans* cells in which RBT1 function is compromised. As noted above in the definition of "compromise" of RBT1 function, it is understood that compromise of RBT1 function also includes, but is not limited to, complete loss of RBT1 function (i.e., knockout). Because *C. albicans* is diploid, compromise of RBT1 fuction may be effected by compromising RBT1 function in either or both RBT1 genes. These cells are useful for providing a known standard for compromise of RBT1 function. Such a standard may be used for comparative purposes when employing the screening methods described herein.

Further, because the rbt1 knockout cell may have low infectivity and thus may be viewed as "inactivated", it is possible that such a cell could be used to elicit an immune response by administration of an amount effective to generate an immune response in an individual. As used herein, an "effective amount" can be administered in one or more than one dose. Accordingly, the invention also provides compositions of these cells, including compositions comprising these cells and a pharmaceutical excipient, as well pharmaceutical compositions comprising these cells. Pharmaceutical excipients are well known in the art and need not be described in detail herein. See, for example, *Remington: The Science and Practice of Pharmacy* (19th edition, 1995), Gennaro, ed.

In some embodiments, compromise of RBT1 function is due to alteration at the DNA level. In one embodiment, compromise of RBT1 function is due to disruption of a single RBT1 gene (i.e., heterozygous), as described in Example 3. In another embodiment, compromise of RBT1 function is due to disruption of both RBT1 genes (i.e., homozygous knockout), as described in Example 3. In another embodiment, disruption of RBT1 is due to site-directed mutagenesis in which the resultant amino acid sequence of Rbt1 is altered. In other embodiments, compromise of RBT1 function is due to alteration of function on, for example, the level of transcription (such as anti-sense). "Anti-sense" as used herein refers to a nucleic acid capable of hybridizing to a portion of an RBT1 RNA (preferably mRNA) by virtue of some sequence complementarity.

In another example, compromise of Rbt1 function may also be accomplished by the over-expression of competitive Rbt1 polypeptide fragments in cells. Such competitive Rbt1 polypeptide fragments would lack at least one fimctional aspect of wild type Rbt1 but would retain the ability to interact with a component(s) of the cell that interact(s) with wild type Rbt1. The presence of such competitive Rbt1 fragments would prevent wild type Rbt1 interactions with cell component(s) and thus result in a compromise of wild type Rbt1 finction. The RBT1 polynucleotides that encode Rbt1 fragments with such competitive activity can be inserted into expression vectors and introduced into cells as described above.

Generally, these cells also contain a selectable marker, such as URA and others described herein. A selectable marker encodes a protein that, for example, confers drug resistance or complements an auxotrophy.

Methods for making such cells, and including techniques for making appropriate genetic manipulations, are known in the art. See, for example, Sherer et al. (1990) *Microb. Rev.* 54:226–241 and Example 3.

Methods Using RBT1 Polynucleotides and Peptides: Cloning Genes and Gene Products Associated with RBT1 Function The invention also provides methods for cloning genes and gene products that are involved in, and/or associated with, a RBT1 function. Because TUP1 function has been shown to play an important role in filamentous formation, and the tup1 knockout is poorly infective, genes that are involved in a TUP1 pathway may well be suitable and useful drug targets. Further, these gene(s) and gene product(s) may provide even more precise, specific targets for drug discovery and development, and hence therapy. The polynucleotides encoding these genes may also be less conserved among fungi and even among various species of Candida, and thus may be especially suitable diagnostic reagents.

As here presented, RBT1 is one gene in a TUP1 finctional pathway. Identification of other genes expressed along with RBT1, that may finction together, in some way, with RBT1, may be important for the above mentioned reasons.

Accordingly, the invention provides methods of isolating genes associated with *C. albicans* RBT1 finction which entail the following step: (a) identification of polynucleotide sequences which are expressed concurrently with RBT1 gene expression. For these methods, the polynucleotides are identified using standard techniques in the art for determining differential expression, such as representational difference analysis (RDA), from cells expressing RBT1 (e.g., cells without TUP1 finction or cells grown in the presence of serum). See Examples 1 and 2 for exemplary conditions.

Preferably, the methods include an additional step (b) of identifying those sequences from step (a) above which are expressed when *C. albicans* is induced to enter filamentous growth. Presumably, this sequence is then considered to be required for filamentous growth. Filamentous growth may be induced, for example, by serum, high temperature, high $CO_2:O_2$ ratio, neutral pH, or nutrient-poor media. In this embodiment, the sequence(s) so identified may be said to be associated with filamentous growth.

Still more preferably, the methods include an additional step of identifying those sequences from step (a) and/or step (b) above which, when deleted, mutated, substituted, or otherwise altered such that the fimction of the expression product is compromised, inhibits filamentous growth in *C. albicans*. In this embodiment, the sequence(s) so identified may be said to be required for filamentous growth, particularly in *C. albicans*.

For these methods, the expression and/or the recovery of RBT1 polynucleotides (and/or Rbt1 polypeptides) is used as a monitor to ensure that the cell growth conditions and the polynucleotide (or polypeptide) isolation conditions are appropriate for the identification of the desired genes and gene products.

The following examples are provided to illustrate but not limit the invention.

EXAMPLES

Example 1

Identification of Polynucleotide Sequences Up-regulated in tup1 Mutant *Candida albicans*

To identify genes up-regulated in *C. albicans* lacking the TUP1 gene, a procedure was performed to isolate cDNA fragments made from mRNA expressed in tup1 mutant cells at higher levels than in wild type *C. albicans*. For this, a Clontech PCR-Select™ cDNA Subtraction Kit was used. This method combined the subtractive process associated with representational difference analysis (Lisitsyn et al., 1993; Hubank and Schatz, 1994) with a suppression PCR step (U.S. Pat. No. 5,565,340)) to increase the probability of identifying rare, differentially expressed mRNA transcripts. For ease of explanation and to conform with the nomenclature found in the references cited, polynucleotides prepared from tup1 mutant cells will be referred to as "tester" mRNA or cDNA and that from wild type cells will be referred to as "driver" mRNA or cDNA.

cDNA synthesis

The cells used in this experiment were wild type *C. albicans* SC5314 (Fonzi et al. (1993) *Genetics* 134:717–728; Gillum et al. (1984) *Mol. General Genetics* 198:179) and tup1 knockout *C. albicans* strain BCa2-10 (Braun et al. (1997) *Science* 277:105–109). PolyA+RNA from these cells was prepared with a Qiagen Oligotex mRNA Maxi Kit.

Except were noted, the procedures and reagents used in the cDNA preparation and subtraction were found in the Clontech PCR-Select™ cDNA Subtraction Kit. The first-strand cDNA was synthesized from 2 μg polya+RNA in a 10 μl reaction that included 1 μM primer 5'-TTTTGTACAAGCTT$_{30}$-3' (SEQ ID NO:5), 200 units MMLV reverse transcriptase, and dNTPs (1 mM each of dATP, dCTP, dGTP, dTTP) in 50 mM Tris-HCl, pH 8.3, 6 mM MgCl$_2$, 75 mM KCl. The reactions were incubated at 42° C. for 1.5 hours. The second-strand of cDNA was synthesized in final reaction volume of 80 μl after the buffer was adjusted to 100 mM KCl, 10 mM (NH$_4$)$_2$SO$_4$, 5 mM MgCl$_2$, 0.15 mM β-NAD, 100 mM Tris-HCl, pH 7.5, 0.05 mg/ml bovine serum albumin (BSA) and 0.2 mM dNTPs by the addition of: DNA polymerase I (24 units), RNAse H (0.8 units), and *E. coli* DNA ligase (4.8 units). After 2 hours at 16° C., 10 units of T4 DNA polymerase was added and the reaction was returned to 16° C. for 30 minutes. Second-strand synthesis was terminated by the addition of EDTA to 10 mM and glycogen to 0.05 mg/ml (EDTA/glycogen mix). Enzymes were removed from the reactions by phenol:chloroform and chloroform extractions and the cDNA concentrated by NH$_4$OAc-ethanol precipitation. The double-stranded cDNAs were resuspended in H$_2$O and digested with RsaI. After the addition of EDTA/glycogen mix, the reactions were extracted with phenol:chloroform and chloroform, and precipitated as before. The cDNA pellets were each resuspended in 6.0 μl H$_2$O.

The suppression PCR technique requires that two populations of tester cDNA exist, each with different polynucleotide adaptors at their ends (listed below). For the adaptor ligation, 1.5 μl of the RsaI-digested tester cDNA was diluted with 7.5 μl of H$_2$O. Each adaptor was ligated in a reaction volume of 10 μl that included 2 μl diluted tester cDNA, 2 mM adaptor, 400 units T4 DNA ligase, 50 mM Tris-HCl, pH 7.8, 10 mM MgCl$_2$, 2 mM DTT, 0.05 mg/ml BSA, and 0.3 mM ATP. After incubation at 16° C. overnight, the reaction was stopped by the addition of the EDTA/glycogen mix and incubation at 72° C. for 5 minutes.

Adaptor 1 (SEQ ID NO:6 and 7):
5'-CTAATACGACTCACTATAGGGCTCGAGCGGCCGCCCGGGCAGGT-3'

3'GGCCCGTCCA-5'

Adaptor 1 (SEQ ID NO:6 and 7):
5'-TGTAGCGTGAAGACGACAGAAAGGGCGTGGTGCGGAGGGCGGT-3'

3'GCCTCCCGCCA-5'

Hybridizations

For the first round of hybridization, each preparation of the adaptor-ligated tester cDNA was mixed with excess driver cDNA in separate reactions. These hybridization reactions combined 1.5 μl of adaptor-ligated tester cDNA with 1.5 μl of RsaI-digested driver cDNA in 1× hybridization buffer (Clontech, Inc.) in a total volume of 4 μl. After being covered in mineral oil and heated at 98° C. for 1.5 minutes, the reactions were incubated at 68° C. for 8 hours. Additional driver cDNA was denatured for the second hybridization by dilution of 1 μl of driver cDNA in 1× hybridization buffer in a total volume of 4 μl and heated to 98° C. for 1.5 minutes. After this DNA was cooled to 68° C., the two tester cDNA hybridization reactions were combined and 1 μl of the denatured driver cDNA mixed in. This second hybridization reaction was incubated at 68° C. overnight, diluted in 200 μl of 20 mM HEPES-HCl, pH 8.3, 50 mM NaCl, 0.2 mM EDTA, pH 8.0, and heated at 75° C. for 7 minutes.

Amplifications

After the subtractive hybridization, desired molecules from the tester cDNA should be double-stranded and have two different ends. Because of this, only the desired molecules should be exponentially amplified when the entire population was subjected to PCR. The first PCR reaction was set up to fill in the adaptor ends as well as amplify the DNA and included 1 μl subtracted cDNA, PCR Primer 1: 5'-CTAATACGACTCACTATAGGGC-3' (SEQ ID NO:10), PCR Primer 2: 5'-TGTAGCGTGAAGACGACAGAA-3' (SEQ ID NO:11), and the Advantage KlenTaq polymerase mix from Clontech in a total volume of 25 μl. After 5 minutes at 75° C. to fill in the single-stranded portion of the adaptors, this preparation underwent 30 cycles of: 30 seconds at 94° C., 30 seconds at 68° C., 2.5 minutes at 72° C. A second PCR was set up using nested primers (from adaptor 1: 5'-TCGAGCGGCCGCCCGGGCAGGT-3' (SEQ ID NO:12); from adaptor 2: 5'-AGGGCGTGGTGCGGAGGGCGGT-3' (SEQ ID NO:13)) and 1 μl of a 1 to 10 dilution of the primary PCR product in a total volume of 25 μl and 10 cycles of: 30 seconds at 94° C., 30 seconds at 68° C., 2.5 minutes. The resulting DNA fragments were 150 to 500 bp in length.

At.this point, DNA in the PCR mixture should have been enriched for the cDNA of transcripts expressed in tup1 mutant cells as compared with wild-type *C. albicans*. The DNA was T/A ligated into a pBluescript® SK+(Stratagene) vector. The T-tailed ends of this vector were created by digestion of the vector with EcoRIV and subsequent treatment with Taq polymerase and dTTP. The ligated products were transformed into DH5αE. coli to create a library of TUP1-repressed cDNAs.

Example 2

Expression Analysis of cDNAs from Library Enriched for TUP1-regulated Sequences

From the cDNA library described in Example 1, clones were randomly picked and their expression in tup1 mutant cells was compared to that in wild type cells by hybridization to RNA blots of both Northern and slot formats. The RNA and blots were prepared by standard protocols. Ausubel et al. (1987). The DNA inserts from these clones were labeled with $^{32}P$ by random priming and DNA polymerase and the blots were hybridized under standard Church conditions. Church et al. (1984) *Proc Natl Acad Sci USA* 81:1991–1995.

A fragment of the RBT1 gene was identified in this screen for TUP1-regulated cDNAs. RBT1 mRNA expression is greatly increased in *C. albicans* cells lacking TUP1 function as compared to wild type cells (compare FIG. 1A (wild type TUP1) with FIG. 1B (mutant tup1Δ)). RBT1 appears to be transcriptionally repressed in the presence of TUP1 finction.

TUP1 control over RBT1 expression was also tested in a strain of *C. albicans* in which TUP1 expression was under control of a maltose-regulated promoter. Such a strain was generated by introducing the MAL2 promoter-TUP1 construct to the mutant tup1Δ *C. albicans* strain. Braun et al. (1997). When these cells are shifted from a medium with maltose to a medium with glucose as the sole carbon source, the maltose promoter is repressed, the TUP1 expression is turned off and so TUP1 activity is depleted, and the RBT1 expression is rapidly induced (FIG. 1C). This rapid induction of RBT1 expression upon depletion of TUP1 function suggests a direct control of RBT1 expression by TUP1.

The tup1 mutant strain of *C. albicans* grows exclusively in filaments. Environmental conditions can induce filamentous growth in wild-type *C. albicans*. Cells grown in YEPD, a medium that favors the blastospore form of growth, will sprout hyphal filaments upon the addition of calf serum. Growth of wild type *C. albicans* in serum also induces the expression of RBT1 mRNA (FIG. 1D). In this experiment, wild type *C. albicans* was grown in YEPD plus 10% calf serum at 37° C. for 0, 30, 60, 90, and 120 minutes. Total RNA was isolated and blotted as described above.

As RBT1 expression was found to be regulated by these conditions (i.e. repressed by TUP1 and expressed by serum stimulation), it is likely to be important for filamentous growth of *C. albicans*.

The sequence of the largest RBT1 cDNA clone identified is found in SEQ ID NO:1 (FIG. 2A). Conceptual translation of the polynucleotide sequence revealed an open reading frame of 108 amino acids (SEQ ID NO:2) (FIG. 2B).

A λ library of *C. albicans* genomic DNA was screened with a radiolabeled RBT1 cDNA probe that contained SEQ ID NO:1. Sequence analysis of one of the identified genomic clones revealed that it contained the entire Rbt1 coding region. The sequence of the genomic clone is found in FIG. 3A and SEQ ID NO:3. Conceptual translation of the open reading frame within the genomic polynucleotide sequence revealed a polypeptide of 750 amino acids (SEQ ID NO:4 and FIG. 3B).

Example 3

Construction of rbt1 Knockout Mutant in *Candida albicans* and Determination of Associated Phenotype(s)

In order to further identify the role of Rbt1 in *C. albicans* filament formation and/or the maintenance of the filamentous form, a strain of *C. albicans* is generated in which RBT1 activity is depleted. The following is a description of one way to knockout the RBT1 genes. Other approaches to achieve this goal are known in the art. This procedure involves modifications of that described in W. A. Fonzi and M. Y. Irwin, (1993) *Genetics* 134:717, Braun et al. (1997), and U.S. Ser. No. 60/051552. In it, both copies of RBT1 are disrupted (*C. albicans* is diploid) in two rounds as described. The *C. albicans* URA3 gene, flanked by two different portions of RBT1 sequence, is cut to remove the vector and is transformed into ura3 *C. albicans* cells. Transformation of *C. albicans* is by a modified lithium acetate technique (R. D. Gietz et al. (1995) *Yeast* 11:355). URA3 transformants are screened by DNA blotting for disruption of one RBT1 gene by homologous recombination. After selecting on 5-fluoroarotic acid plates for ura3 "pop-out" revertants, a second cycle of transformation is performed. DNA blotting demonstrates the successive disruption of both copies of the RBT1 gene. All *C. albicans* strains used share the SC5314 background.

The disruption consists of a large deletion that excises most of the RBT1 gene as well as DNA upstream of the open reading frame. To ensure that the phenotypes of the cells result from loss of RBT1 finction rather than loss of the upstream DNA or other features of the locus separate from the RBT1 open reading frame, the second round of disruption is also carried out with a DNA fragment that carries *C. albicans* rbt1 with an N-terminal frame-shift mutation instead of a large deletion. Wild type *C. albicans* phenotypes are fully restored by insertion of a wild type copy of the RBT1 gene linked to an adjacent URA3 marker back into the disrupted locus.

The growth of mutant rbt1 and wild type *C. albicans* are compared on various media and under various environmental conditions that favor either blastospore or filamentous growth. Infectivity and virulence of *C. albicans* cells containing the rbt knockout are measured in mice. An example of one way to test the infectivity and virulence of these strains of *C. albicans* is to inoculate groups of 4 inbred CAB/J(H-2K) mice vaginally and/or orally with wild type *C. albicans* or rbt1 knockout *C. albicans*. U.S. Ser. No. 60/051552.; de Bernardis (1993) *Infect. Immun.* 61:1500–1508; Marquis (1986) *J. Infect. Dis.* 154:906–909; Shepherd (1985) *Infect. Immun.* 50:541–544; Fidel et al. (1993) *Immun.* 61:1990–1995; Fidel et al (1996) *J. Infec. Disease* 173(2):425–431. At various time points after inoculation, assessments are made regarding the amount of *C. albicans* in various tissues, the degree of pathology associated with the infection, if any, and the survival rates of the mice.

Example 4

Overexpression of RBT1 and RBT1 Fragments in *C. albicans* and Determination of Associated Phenotype(s)

Loss of TUP1 activity in *C. albicans* results in growth in filaments and the concomitant activation of expression of RBT1 and other genes. To determine whether RBT1 expression alone can induce filamentous growth, RBT1 is expressed in wild type *C. albicans* under conditions associated with blastospore growth. For example, the RBT1 open reading frame is cloned into a vector under the control of a promoter transcriptionally active in *C. albicans* (e.g., the promoter of the MAL2 gene). After this construct is introduced into *C. albicans* cells and the cells identified that carry the construct, the cells are grown under conditions that do not induce filamentous growth in wild type cells but do induce expression of the RBT1 expression construct (e.g., maltose). The cells are examined for the expression of Rbt1 and their morphology is observed. If RBT1 expression is found to induce filamentous growth, this approach is then used with fragments of the RBT1 to determine the domains of the protein that are involved in filamentous growth.

To determine whether the *C. albicans* RBT1 gene is functional in another yeast, *C. albicans* RBT1 is expressed under control of a promoter that is functional in the host yeast cell. For example, in the case of *S. cerevisiae*, *C. albicans* RBT1 is expressed under a galactose controlled promoter. The *C. albicans* RBT1 open reading frame is cloned into the CEN/ARS/URA3/Gal1-10 expression vector pRD53 (gift of R. Deshaies, Cal Tech) to form the *S. cerevisiae* expression plasmid. Transformations of *S. cerevisiae* are done by a modified lithium acetate technique (R. D. Gietz et al. (1995) *Yeast* 11:355; J. Hill et al. (1991) *Nucleic Acids Res.* 19:5791). To assess RBT1 finction, *S. cerevisiae* carrying the RBT1 construct are grown under conditions that do not induce filamentous growth in wild type cells. The cells are examined for the expression of Rbt1 and their morphology is observed. Many types of yeast, and the methods to work with them, have been mentioned above and are known in the art.

Example 5

Screening Candidate Anti-fungal Agents Using RBT1

As described in this application, TUP1 function controls the morphology of *C. albicans* and the expression of RBT1 is an indication of Tup1 activity. Thus, RBT1 expression is an indicator of morphological state (i.e., RBT1 expressed, cells grow in filaments; RBT1 not expressed, cells grow as blastospores) and can be used to identify agents that modulate the morphological transition of *C. albicans*.

In an example to identify such agents, an RBT1-green fluorescent protein (GFP) hybrid gene is assembled in which the expression of GFP is under the control of the RBT1 regulatory elements and this hybrid gene is stably introduced into *C. albicans*.

To screen for agents that shift the morphology to the filamentous form, cells that carry the RBT1-GFP hybrid gene are grown in standard media and an agent to be tested is added (control cells receive no agent). After a suitable time, the cell suspensions are checked for GFP fluorescence. These assays may be rapidly and conveniently performed in microtiter plates, using in a small amount of media and agent to be tested in each well with the cells. Agents are identified by their ability to elicit GFP fluorescence. Such agents can then be tested for their ability to elicit filamentous growth in the standard, but more time consuming, assays.

As an example of a screen for agents that shift the morphology to the blastospore form, cells that carry the RBT1-GFP hybrid gene are grown in conditions that induce filamentous growth, e.g. in the presence of 10% calf serum, and the agent to be tested is added. Control cells receive no agent and, after a suitable time, the cell suspensions are checked for GFP fluorescence. Agents are identified by their ability to decrease the amount of GFP fluorescence relative to the control.

After the identification of agents using cells in culture, they are tested for their effect on animals infected with *C. albicans*. Mice are inoculated with wild type *C. albicans*. The agent is administered to the animals (control animals receive no agent) and the levels of GFP fluorescence at sites of accumulation and/or growth of *C. albicans* is an indicator of the agent's efficacy in the animal. The degree of pathology is then monitored and compared to the morphological forms of *C. albicans* in the infected tissue.

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

We claim:

1. An isolated polynucleotide comprising a sequence encoding an Rbt1 polypeptide from *C. albicans*, wherein the Rbt1 polypeptide is at least 10 amino acids in length and is depicted within SEQ ID NO:4.

2. An isolated polynucleotide of claim 1, wherein the Rbt1 polypeptide is a sequence from about amino acid 480 to about amino acid 496 of SEQ ID NO:4.

3. An isolated polynucleotide of claim 1, wherein the Rbt1 polypeptide is a sequence from about amino acid 1 to about amino acid 23 of SEQ ID NO:4.

4. An isolated polynucleotide of claim 1, wherein the Rbt1 polypeptide is SEQ ID NO:2.

5. An isolated polynucleotide of claim 1, wherein the Rbt1 polypeptide is SEQ ID NO:4.

6. An isolated polynucleotide comprising nucleotides from about 2054 to about 2104 of SEQ ID NO:3.

7. An isolated polynucleotide comprising nucleotides from about 617 to about 685 of SEQ ID NO:3.

8. An isolated polynucleotide comprising nucleotides from about 617 to about 2866 of SEQ ID NO:3.

9. An isolated polynucleotide comprising a region of at least 20 contiguous nucleotides, said region having at least 75% sequence identity with a sequence depicted in SEQ ID NO:3, wherein expression of a polynucleotide containing said region is increased during conversion of *C. albicans* to filamentous form.

10. An isolated polynucleotide of claim 9, wherein the region has at least 85% sequence identity with a sequence depicted in SEQ ID NO:3.

11. An isolated polynucleotide of claim 9, wherein expression of a polynucleotide containing said region is regulated by TUP1 in *C. albicans*.

12. A cloning vector comprising the polynucleotide of claim 1.

13. A cloning vector comprising the polynucleotide of claim 5.

14. A cloning vector comprising the polynucleotide of claim 9.

15. An expression vector comprising the polynucleotide of claim 1.

16. An expression vector comprising the polynucleotide of claim 5.

17. An expression vector comprising the polynucleotide of claim 9.

18. A h ost c ell comprising the polynucleotide of claim 1.

19. A host cell comprising the polynucleotide of claim 5.

20. A host cell comprising the polynucleotide of claim 9.

21. The host cell of claim 18, wherein the host cell is *C. albicans*.

22. The host cell of claim 19, wher ein the host cll is *C. albicans*.

23. The host cell of claim 20, wherein the host cell is *C. albicans*.

24. A composition comprising the polynucleotide of claim 1.

25. An isolated polypeptide comprising an Rbt1 polypeptide sequence from *C. albicans*, wherein the polypeptide comprises about amino acid 480 to about amino acid 496 of SEQ ID NO:4.

26. An isolated polypeptide comprising an Rbt1 polypeptide sequence from *C. albicans*, wherein the polypeptide comprises about amino acid 1 to about amino acid 23 of SEQ ID NO:4.

27. The isolated polypeptide of claim 25, wherein the polypeptide comprises the sequence of SEQ ID NO:2.

28. The isolated polypeptide of claim 25, wherein the polypeptide comprises the sequence of SEQ ID NO:4.

29. An isolated polypeptide comprising at least 10 contiguous amino acids which have at least 70% sequence identity to a sequence depicted in SEQ ID NO:4, and wherein expression of said at least 10 contiguous amino acids is increased during conversion of *C. albicans* to filamentous form.

30. An isolated polypeptide of claim 29, wherein expression of said at least 10 contiguous amino acids is regulated by TUP1 in *C. albicans*.

31. A composition comprising the polypeptide of claim 25.

32. A composition comprising the polypeptide of claim 26.

33. A composition comprising the polypeptide of claim 29.

34. A purified antibody capable of specifically binding to a polypeptide of claim 25.

35. A monoclonal antibody capable of specifically binding to a polypeptide of claim 25.

36. A method for detecting a polynucleotide from *C. albicans* in a biological sample comprising the steps of (a) contacting a polynucleotide from *C. albicans* in said sample with the polynucleotide of claim 1 under conditions that permit the formation of a stable duplex; and (b) detecting a stable duplex formed in step (a).

37. A method for detecting a polynucleotide from *C. albicans* in a biological sample comprising the steps of (a) conducting an amplification reaction on a polynucleotide from *C. albicans* in said sample using a primer consisting of a fragment of the polynucleotide sequence of SEQ ID NO:3; and (b) detecting the presence of amplified copies of the polynucleotide.

38. A method for detecting an anti-*C. albicans* Rbt1 antibody in a biological sample, comprising the steps of (a) contacting an antibody from the sample with a polypeptide of claim 25 under conditions which permit formation of a stable antigen-antibody complex; and (b) detecting said stable complexes formed in step (a).

39. A method for detecting a *C. albicans* Rbt1 polypeptide in a biological sample, comprising the steps of: (a) contacting a polypeptide from the biological sample with the antibody of claim 35 under conditions that permit the formation of a stable antigen-antibody complex; and (b) detecting said stable complexes formed in step (a).

40. A method for identifying an agent that may control virulence of *C. albicans*, said method comprising:

(a) contacting at least one agent to be tested with a *C. albicans* cell that has RBT1 finction;

(b) analyzing at least one characteristic which is associated with a modulation of RBT1 function in said host cell, wherein an agent is identified by its ability to elicit at least one such characteristic.

41. A composition for controlling virulence of *C. albicans* comprising an agent identified in the method of claim 40.

42. A kit for detection or quantification of a polynucleotide comprising a *C. albicans* RBT1 polynucleotide or a fragment thereof in a biological sample, said kit comprising the polynucleotide of claim 1 in suitable packaging.

43. A kit for detection or quantification of a *C. albicans* polypeptide in a biological sample, said kit comprising the antibody of claim 35 in suitable packaging.

44. A kit for detection or quantification of an anti-*C. albicans* antibody in a biological sample, said kit comprising the polypeptide of claim 25 in suitable packaging.

45. A method of isolating a polynucleotide sequence from *C. albicans* that is associated with morphologic transition, said method comprising identifying a transcribed polynucleotide which is up-regulated upon *C. albicans* RBT1 expression.

46. A method of claim 45, firther comprising identifying those polynucleotides identified in claim 45 which are transcribed when *C. albicans* is induced to enter filamentous growth formation.

47. A method of claim 46, fiurther comprising identifying those polynucleotides identified in claim 46 which inhibit filamentous growth in *C. albicans* when expression of those polynucleotides is compromised.

48. A method of modulating morphological transition of *C. albicans*, comprising administering an agent capable of modulating *C. albicans* RBT1 function.

49. A method of claim 48, wherein RBT1 function is modulated by disrupting at least one RBT1 gene in *C. albicans*.

50. A method of claim 48, wherein RBT1 finction is modulated by contacting a *C. albicans* cell with an agent identified in the method of claim 40.

51. The method of claim 40, comprising analyzing RBT1 transcription.

52. The method of claim 40, comprising analyzing RBT1 translation.

53. The method of claim 40, comprising analyzing RBT1 regulation during conversion between morphological forms of *C. albicans*.

54. The method of claim 40, comprising analyzing RBT1 regulation during maintenance of the filamentous form of *C. albicans*.

55. The method of claim 45, wherein RBT1 function comprises transcription.

56. The method of claim 45, wherein RBT1 function comprises translation.

57. The method of claim 45, wherein RBT1 function comprises regulation during conversion between morphological forms of *C. albicans*.

58. The method of claim 45, wherein RBT1 function comprises regulation during maintenance of the filamentous form of *C. albicans*.

59. An isolated *C. albicans* cell in which RBT1 function is compromised.

\* \* \* \* \*

SEQUENCE LISTING

```
<160> NUMBER OF SEQ ID NOS: 13

<210> SEQ ID NO 1
<211> LENGTH: 325
<212> TYPE: DNA
<213> ORGANISM: Candida albicans
<220> FEATURE:
<221> NAME/KEY: CDS
<222> LOCATION: (2)...(325)

<400> SEQUENCE: 1 t gcc cca gaa tca tct gct cca gaa tct agt gcc cca gaa tca tct gca      49
  Ala Pro Glu Ser Ser Ala Pro Glu Ser Ser Ala Pro Glu Ser Ser Ala
    1               5                  10                  15 cca gtc act gaa aca cca act ggt cca gtt tcc act gtt act gag caa       97
Pro Val Thr Glu Thr Pro Thr Gly Pro Val Ser Thr Val Thr Glu Gln
             20                  25                  30 tca aag acc atc gtc acc atc acc tca tgc tcc aac aat gca tgc agt       145
Ser Lys Thr Ile Val Thr Ile Thr Ser Cys Ser Asn Asn Ala Cys Ser
         35                  40                  45 gaa tct aag gtc acc act ggt gtt gtt gtt gtt aca tct gaa gat act       193
```

```
                                                                      -continued gtt tac act aca ttc tgt cca tta act gaa act act cca gct act gaa    241
Glu Ser Lys Val Thr Thr Gly Val Val Val Thr Ser Glu Asp Thr
         50                  55                  60

Val Tyr Thr Thr Phe Cys Pro Leu Thr Glu Thr Thr Pro Ala Thr Glu
 65                  70                  75                  80 tca gcc cca gaa tca tct gca cca gcc act gaa tca gtt cca gct act    289
Ser Ala Pro Glu Ser Ser Ala Pro Ala Thr Glu Ser Val Pro Ala Thr
                 85                  90                  95 gaa agt gct cca gtt gct cca gaa tca tct gca cca                    325
Glu Ser Ala Pro Val Ala Pro Glu Ser Ser Ala Pro
                100                 105

<210> SEQ ID NO 2
<211> LENGTH: 108
<212> TYPE: PRT
<213> ORGANISM: Candida albicans

<400> SEQUENCE: 2

Ala Pro Glu Ser Ser Ala Pro Glu Ser Ser Ala Pro Glu Ser Ser Ala
 1               5                  10                  15

Pro Val Thr Glu Thr Pro Thr Gly Pro Val Ser Thr Val Thr Glu Gln
                 20                  25                  30

Ser Lys Thr Ile Val Thr Ile Thr Ser Cys Ser Asn Asn Ala Cys Ser
             35                  40                  45

Glu Ser Lys Val Thr Thr Gly Val Val Val Thr Ser Glu Asp Thr
         50                  55                  60

Val Tyr Thr Thr Phe Cys Pro Leu Thr Glu Thr Thr Pro Ala Thr Glu
 65                  70                  75                  80

Ser Ala Pro Glu Ser Ser Ala Pro Ala Thr Glu Ser Val Pro Ala Thr
                 85                  90                  95

Glu Ser Ala Pro Val Ala Pro Glu Ser Ser Ala Pro
                100                 105

<210> SEQ ID NO 3
<211> LENGTH: 3168
<212> TYPE: DNA
<213> ORGANISM: Candida albicans
<220> FEATURE:
<221> NAME/KEY: CDS
<222> LOCATION: (617)...(2866)

<400> SEQUENCE: 3
tatctttgtc attataaggc gtgttttggt tttggttttg gggttttgtt ttttcgtttt      60
taatgcaaga atcttagctt tgttttgcat gattttcggg tttaatgcat agtgcgatat     120
ttgataaccc tggcacagca tctttgtttc cactaatgtt cattgcattt ttaaaatttt     180
tcagtaccct acgccaatta aaccaaatac cctccaatgc tttgtctcgc aataattaaa     240
cattttcaag aatgttctct tttttagatt tttcaattct ttgttttta atcacaaata      300 tgaaaacatt ttcgacagat tcgttttagt attttttataa ttctacacaa agttaaattt    360
ttcacactgt tttaagttcg actttggaat gttaatgctt ctattttttc aattcggatc    420
ttgaaagaca attcccgtt gatttcaaca attaatcaat ggttataata tgatcaaatt     480
actttcccaa aaactataaa taaggtaag atttaccgga ttttgaactt gtaattttct     540
tattttccta tcccatcaac aagatcaaac aaaatacaaa tctcgtatta ttcattcgct     600
ttaattttta tcaact atg aga ttt gca act gcc caa ctc gct gcc ctc gct    652
                  Met Arg Phe Ala Thr Ala Gln Leu Ala Ala Leu Ala
                   1               5                  10
```

-continued

| | | | | | | | | | | | | | | | | |
|---|---|---|---|---|---|---|---|---|---|---|---|---|---|---|---|---|
| tac | tac | att | tta | tcc | act | gag | gct | act | ttc | cca | tta | ttg | ggt | gac | atc | 700 |
| Tyr | Tyr | Ile | Leu | Ser | Thr | Glu | Ala | Thr | Phe | Pro | Leu | Leu | Gly | Asp | Ile | |
| | | 15 | | | | | 20 | | | | | 25 | | | | |
| ttt | aat | tgt | att | cca | cac | aac | act | cct | cct | gtc | tgt | act | gac | ttg | ggt | 748 |
| Phe | Asn | Cys | Ile | Pro | His | Asn | Thr | Pro | Pro | Val | Cys | Thr | Asp | Leu | Gly | |
| | 30 | | | | | 35 | | | | | 40 | | | | | |
| ctt | tac | cac | gat | agc | tcc | att | tcc | ctt | agt | ggt | tcc | aag | aac | aag | aga | 796 |
| Leu | Tyr | His | Asp | Ser | Ser | Ile | Ser | Leu | Ser | Gly | Ser | Lys | Asn | Lys | Arg | |
| 45 | | | | | 50 | | | | | 55 | | | | | 60 | |
| gaa | gct | gaa | att | gtc | aat | gaa | gat | ggt | aca | att | gaa | aag | aga | act | ttt | 844 |
| Glu | Ala | Glu | Ile | Val | Asn | Glu | Asp | Gly | Thr | Ile | Glu | Lys | Arg | Thr | Phe | |
| | | | | 65 | | | | | 70 | | | | | 75 | | |
| gga | agc | gct | ggt | gta | aat | gcc | ggt | ttc | aat | gcc | gca | ttt | gtc | gtg | tct | 892 |
| Gly | Ser | Ala | Gly | Val | Asn | Ala | Gly | Phe | Asn | Ala | Ala | Phe | Val | Val | Ser | |
| | | | 80 | | | | | 85 | | | | | 90 | | | |
| aat | gcc | aaa | aaa | tta | tct | gac | ggt | tct | tat | ggt | att | gat | tgt | aac | ttc | 940 |
| Asn | Ala | Lys | Lys | Leu | Ser | Asp | Gly | Ser | Tyr | Gly | Ile | Asp | Cys | Asn | Phe | |
| | | 95 | | | | | 100 | | | | | 105 | | | | |
| aag | agt | gat | tct | tct | gtc | caa | ttg | aac | ctg | gcc | ttt | ggt | aaa | aaa | gtt | 988 |
| Lys | Ser | Asp | Ser | Ser | Val | Gln | Leu | Asn | Leu | Ala | Phe | Gly | Lys | Lys | Val | |
| | 110 | | | | | 115 | | | | | 120 | | | | | |
| aaa | caa | ttg | agt | atc | acc | ggt | act | ggt | tat | tct | gat | att | tca | tta | tta | 1036 |
| Lys | Gln | Leu | Ser | Ile | Thr | Gly | Thr | Gly | Tyr | Ser | Asp | Ile | Ser | Leu | Leu | |
| 125 | | | | | 130 | | | | | 135 | | | | | 140 | |
| gga | aat | gtt | gct | aat | cca | ttt | gaa | tgg | tca | gct | tcc | ttg | aaa | gtc | aaa | 1084 |
| Gly | Asn | Val | Ala | Asn | Pro | Phe | Glu | Trp | Ser | Ala | Ser | Leu | Lys | Val | Lys | |
| | | | | 145 | | | | | 150 | | | | | 155 | | |
| gca | gaa | att | gtt | aaa | gga | aaa | tgt | tgt | ctt | cca | tca | ggt | ttc | aga | atc | 1132 |
| Ala | Glu | Ile | Val | Lys | Gly | Lys | Cys | Cys | Leu | Pro | Ser | Gly | Phe | Arg | Ile | |
| | | | 160 | | | | | 165 | | | | | 170 | | | |
| gtt | aca | gat | ttc | gaa | agc | aac | tgt | cct | gaa | ttt | gat | gcc | atc | aaa | caa | 1180 |
| Val | Thr | Asp | Phe | Glu | Ser | Asn | Cys | Pro | Glu | Phe | Asp | Ala | Ile | Lys | Gln | |
| | | 175 | | | | | 180 | | | | | 185 | | | | |
| ttt | ttt | ggc | agt | tct | caa | ata | att | tac | aaa | gtc | aat | gcc | gtt | tct | aac | 1228 |
| Phe | Phe | Gly | Ser | Ser | Gln | Ile | Ile | Tyr | Lys | Val | Asn | Ala | Val | Ser | Asn | |
| | 190 | | | | | 195 | | | | | 200 | | | | | |
| gca | att | ggt | act | ttt | gat | gct | tct | gca | tta | ttc | aat | gct | caa | gtc | aaa | 1276 |
| Ala | Ile | Gly | Thr | Phe | Asp | Ala | Ser | Ala | Leu | Phe | Asn | Ala | Gln | Val | Lys | |
| 205 | | | | | 210 | | | | | 215 | | | | | 220 | |
| gcc | ttc | cct | gcc | aag | aga | gaa | tta | gat | gaa | ttt | gaa | gaa | tta | agt | aac | 1324 |
| Ala | Phe | Pro | Ala | Lys | Arg | Glu | Leu | Asp | Glu | Phe | Glu | Glu | Leu | Ser | Asn | |
| | | | | 225 | | | | | 230 | | | | | 235 | | |
| gat | ggt | gtt | act | cac | agc | aag | aga | act | ttg | ggt | ttg | ctt | ttg | ggt | ttg | 1372 |
| Asp | Gly | Val | Thr | His | Ser | Lys | Arg | Thr | Leu | Gly | Leu | Leu | Leu | Gly | Leu | |
| | | | 240 | | | | | 245 | | | | | 250 | | | |
| ctt | aag | aaa | gtt | act | ggt | gga | tgt | gat | act | tta | caa | caa | ttc | tgt | tgg | 1420 |
| Leu | Lys | Lys | Val | Thr | Gly | Gly | Cys | Asp | Thr | Leu | Gln | Gln | Phe | Cys | Trp | |
| | | 255 | | | | | 260 | | | | | 265 | | | | |
| gac | tgt | caa | tgt | gac | acc | cca | tct | cca | tca | act | acc | acc | gta | agt | act | 1468 |
| Asp | Cys | Gln | Cys | Asp | Thr | Pro | Ser | Pro | Ser | Thr | Thr | Thr | Val | Ser | Thr | |
| | 270 | | | | | 275 | | | | | 280 | | | | | |
| tca | tct | gct | cca | tct | act | tcc | cca | gaa | tca | tct | gct | cca | tct | act | act | 1516 |
| Ser | Ser | Ala | Pro | Ser | Thr | Ser | Pro | Glu | Ser | Ser | Ala | Pro | Ser | Thr | Thr | |
| 285 | | | | | 290 | | | | | 295 | | | | | 300 | |
| aca | gtt | acc | act | tca | tct | tct | cca | gtt | act | tct | cca | gaa | tct | agt | gtt | 1564 |
| Thr | Val | Thr | Thr | Ser | Ser | Ser | Pro | Val | Thr | Ser | Pro | Glu | Ser | Ser | Val | |
| | | | | 305 | | | | | 310 | | | | | 315 | | |
| cca | gaa | act | act | acc | gtt | act | act | tca | tct | gtc | cca | gaa | act | act | cca | 1612 |
| Pro | Glu | Thr | Thr | Thr | Val | Thr | Thr | Ser | Ser | Val | Pro | Glu | Thr | Thr | Pro | |
| | | 320 | | | | | 325 | | | | | 330 | | | | |

-continued

```
gaa tca tca gct cca gaa acc acc aca gtt act act tca tct gtt cct    1660
Glu Ser Ser Ala Pro Glu Thr Thr Thr Val Thr Thr Ser Ser Val Pro
        335                 340                 345 tct act acc cca gag tct tct gct cca gaa acc act cca gaa tca tca    1708
Ser Thr Thr Pro Glu Ser Ser Ala Pro Glu Thr Thr Pro Glu Ser Ser
        350                 355                 360 gct cca gaa tct agt gtt cca gaa tca tca gct cca gaa acc act cca    1756
Ala Pro Glu Ser Ser Val Pro Glu Ser Ser Ala Pro Glu Thr Thr Pro
365                 370                 375                 380 gaa tca tca gct cca gaa tct agt gtt cca gaa tca tca gct cca gaa    1804
Glu Ser Ser Ala Pro Glu Ser Ser Val Pro Glu Ser Ser Ala Pro Glu
                385                 390                 395 act gaa act gaa acc act cca act gct cac tta act act act act gct    1852
Thr Glu Thr Glu Thr Thr Pro Thr Ala His Leu Thr Thr Thr Thr Ala
            400                 405                 410 caa act act act gtt ata act gtt act tca tgc tct aac aat gct tgt    1900
Gln Thr Thr Thr Val Ile Thr Val Thr Ser Cys Ser Asn Asn Ala Cys
            415                 420                 425 agc aaa act gaa gta acc aca ggt gtt gtt gtt gtc act tct gaa gat    1948
Ser Lys Thr Glu Val Thr Thr Gly Val Val Val Val Thr Ser Glu Asp
        430                 435                 440 act att tac act acc ttc tgt cca tta act gaa acc acc cca gtt cct    1996
Thr Ile Tyr Thr Thr Phe Cys Pro Leu Thr Glu Thr Thr Pro Val Pro
445                 450                 455                 460 tca agt gtt gat tct act tca gtc act tct gct cca gaa acc acc cca    2044
Ser Ser Val Asp Ser Thr Ser Val Thr Ser Ala Pro Glu Thr Thr Pro
                465                 470                 475 gaa tct act gcc cca gaa tca tct gct cca gaa tct agt gcc cca gaa    2092
Glu Ser Thr Ala Pro Glu Ser Ser Ala Pro Glu Ser Ser Ala Pro Glu
            480                 485                 490 tca tct gca cca gtc act gaa aca cca act ggt cca gtt tcc act gtt    2140
Ser Ser Ala Pro Val Thr Glu Thr Pro Thr Gly Pro Val Ser Thr Val
        495                 500                 505 act gag caa tca aag acc atc gtc acc atc acc tca tgc tcc aac aat    2188
Thr Glu Gln Ser Lys Thr Ile Val Thr Ile Thr Ser Cys Ser Asn Asn
    510                 515                 520 gca tgc agt gaa tct aag gtc acc act ggt gtt gtt gtt gtt aca tct    2236
Ala Cys Ser Glu Ser Lys Val Thr Thr Gly Val Val Val Val Thr Ser
525                 530                 535                 540 gaa gat act gtt tac act aca ttc tgt cca tta act gaa act act cca    2284
Glu Asp Thr Val Tyr Thr Thr Phe Cys Pro Leu Thr Glu Thr Thr Pro
                545                 550                 555 gct act gaa tca gcc cca gaa tca tct gca cca gcc act gaa tca gtt    2332
Ala Thr Glu Ser Ala Pro Glu Ser Ser Ala Pro Ala Thr Glu Ser Val
            560                 565                 570 cca gct act gaa agt gct cca gtt gct cca gaa tca tct gca cca ggt    2380
Pro Ala Thr Glu Ser Ala Pro Val Ala Pro Glu Ser Ser Ala Pro Gly
        575                 580                 585 act gaa acc gca cca gct acc gaa tca gct cct gcc act gaa agt tct    2428
Thr Glu Thr Ala Pro Ala Thr Glu Ser Ala Pro Ala Thr Glu Ser Ser
    590                 595                 600 cca gtt gct cca ggt act gaa tct tcc cca gtt gcc cca gaa tca tca    2476
Pro Val Ala Pro Gly Thr Glu Ser Ser Pro Val Ala Pro Glu Ser Ser
605                 610                 615                 620 gca cca gct act gaa tca gca cca gcc acc gaa tct tcc cca gtt gct    2524
Ala Pro Ala Thr Glu Ser Ala Pro Ala Thr Glu Ser Ser Pro Val Ala
                625                 630                 635 cca ggt act gaa acc act cca gct act cca ggt gct gaa tca act cca    2572
Pro Gly Thr Glu Thr Thr Pro Ala Thr Pro Gly Ala Glu Ser Thr Pro
```

-continued

```
                 640                 645                 650
gtt gct cca gtt gcc cca gaa tca tca gct cca gct gtt gaa tct tct         2620
Val Ala Pro Val Ala Pro Glu Ser Ser Ala Pro Ala Val Glu Ser Ser
                 655                 660                 665 cca gtt gct cca ggt gtc gaa act act cca gtt gca cca gtt gct cct         2668
Pro Val Ala Pro Gly Val Glu Thr Thr Pro Val Ala Pro Val Ala Pro
         670                 675                 680 tct acc act gca aaa act agt gct ctc gtc tct acg act gag ggt act         2716
Ser Thr Thr Ala Lys Thr Ser Ala Leu Val Ser Thr Thr Glu Gly Thr
685                 690                 695                 700 att cca act aca tta gaa tct gtt cct gcc att caa cca tct gct aac         2764
Ile Pro Thr Thr Leu Glu Ser Val Pro Ala Ile Gln Pro Ser Ala Asn
                 705                 710                 715 tcc tca tac act att gct tca gtc tct tca ttc gaa ggt gct ggt aac         2812
Ser Ser Tyr Thr Ile Ala Ser Val Ser Ser Phe Glu Gly Ala Gly Asn
                 720                 725                 730 aac atg aga tta act tat ggt gct gct att att ggt ctt gct gca ttc         2860
Asn Met Arg Leu Thr Tyr Gly Ala Ala Ile Ile Gly Leu Ala Ala Phe
                 735                 740                 745 ttg atc taattctagt tactgatact atatctttt cttttctgt ttggatttct            2916
Leu Ile
    750 actaattaca ttttcaatt ttcggttttc aatattatga caaaggttat tgtattgaat        2976 atttactttg gtacataaaa aaaagttggt gcttttttc ttttagaatt gttttgttta        3036 gatttcgtat ttcttctta ttctgctttt cattttcggt gtatagatta caacttacaa       3096 taaataccat ttttttcta ttaaattttt catcacattg attagttttc aacttgaaaa       3156 gaattcgaat tg                                                            3168

<210> SEQ ID NO 4
<211> LENGTH: 750
<212> TYPE: PRT
<213> ORGANISM: Candida albicans

<400> SEQUENCE: 4

Met Arg Phe Ala Thr Ala Gln Leu Ala Ala Leu Ala Tyr Tyr Ile Leu
 1               5                  10                  15

Ser Thr Glu Ala Thr Phe Pro Leu Leu Gly Asp Ile Phe Asn Cys Ile
             20                  25                  30

Pro His Asn Thr Pro Pro Val Cys Thr Asp Leu Gly Leu Tyr His Asp
         35                  40                  45

Ser Ser Ile Ser Leu Ser Gly Ser Lys Asn Lys Arg Glu Ala Glu Ile
     50                  55                  60

Val Asn Glu Asp Gly Thr Ile Glu Lys Arg Thr Phe Gly Ser Ala Gly
 65                  70                  75                  80

Val Asn Ala Gly Phe Asn Ala Ala Phe Val Ser Asn Ala Lys Lys
                 85                  90                  95

Leu Ser Asp Gly Ser Tyr Gly Ile Asp Cys Asn Phe Lys Ser Asp Ser
            100                 105                 110

Ser Val Gln Leu Asn Leu Ala Phe Gly Lys Lys Val Lys Gln Leu Ser
        115                 120                 125

Ile Thr Gly Thr Gly Tyr Ser Asp Ile Ser Leu Leu Gly Asn Val Ala
    130                 135                 140

Asn Pro Phe Glu Trp Ser Ala Ser Leu Lys Val Lys Ala Glu Ile Val
145                 150                 155                 160

Lys Gly Lys Cys Cys Leu Pro Ser Gly Phe Arg Ile Val Thr Asp Phe
```

```
                    165                 170                 175
Glu Ser Asn Cys Pro Glu Phe Asp Ala Ile Lys Gln Phe Phe Gly Ser
                180                 185                 190
Ser Gln Ile Ile Tyr Lys Val Asn Ala Val Ser Asn Ala Ile Gly Thr
            195                 200                 205
Phe Asp Ala Ser Ala Leu Phe Asn Ala Gln Val Lys Ala Phe Pro Ala
        210                 215                 220
Lys Arg Glu Leu Asp Glu Phe Glu Leu Ser Asn Asp Gly Val Thr
225                 230                 235                 240
His Ser Lys Arg Thr Leu Gly Leu Leu Gly Leu Leu Lys Lys Val
                245                 250                 255
Thr Gly Gly Cys Asp Thr Leu Gln Gln Phe Cys Trp Asp Cys Gln Cys
                260                 265                 270
Asp Thr Pro Ser Pro Ser Thr Thr Val Ser Thr Ser Ala Pro
        275                 280                 285
Ser Thr Ser Pro Glu Ser Ser Ala Pro Ser Thr Thr Thr Val Thr Thr
        290                 295                 300
Ser Ser Ser Pro Val Thr Ser Pro Glu Ser Val Pro Glu Thr Thr
305                 310                 315                 320
Thr Val Thr Thr Ser Ser Val Pro Glu Thr Pro Glu Ser Ser Ala
                325                 330                 335
Pro Glu Thr Thr Thr Val Thr Thr Ser Ser Val Pro Ser Thr Thr Pro
                340                 345                 350
Glu Ser Ser Ala Pro Glu Thr Thr Pro Glu Ser Ser Ala Pro Glu Ser
        355                 360                 365
Ser Val Pro Glu Ser Ser Ala Pro Glu Thr Thr Pro Glu Ser Ser Ala
        370                 375                 380
Pro Glu Ser Ser Val Pro Glu Ser Ser Ala Pro Glu Thr Glu Thr Glu
385                 390                 395                 400
Thr Thr Pro Thr Ala His Leu Thr Thr Thr Thr Ala Gln Thr Thr Thr
                405                 410                 415
Val Ile Thr Val Thr Ser Cys Ser Asn Asn Ala Cys Ser Lys Thr Glu
                420                 425                 430
Val Thr Thr Gly Val Val Val Thr Ser Glu Asp Thr Ile Tyr Thr
                435                 440                 445
Thr Phe Cys Pro Leu Thr Glu Thr Thr Pro Val Pro Ser Ser Val Asp
        450                 455                 460
Ser Thr Ser Val Thr Ser Ala Pro Glu Thr Thr Pro Glu Ser Thr Ala
465                 470                 475                 480
Pro Glu Ser Ser Ala Pro Glu Ser Ser Ala Pro Glu Ser Ser Ala Pro
                485                 490                 495
Val Thr Glu Thr Pro Thr Gly Pro Val Ser Thr Val Thr Glu Gln Ser
                500                 505                 510
Lys Thr Ile Val Thr Ile Thr Ser Cys Ser Asn Asn Ala Cys Ser Glu
            515                 520                 525
Ser Lys Val Thr Thr Gly Val Val Val Thr Ser Glu Asp Thr Val
        530                 535                 540
Tyr Thr Thr Phe Cys Pro Leu Thr Glu Thr Thr Pro Ala Thr Glu Ser
545                 550                 555                 560
Ala Pro Glu Ser Ser Ala Pro Ala Thr Glu Ser Val Pro Ala Thr Glu
                565                 570                 575
Ser Ala Pro Val Ala Pro Glu Ser Ser Ala Pro Gly Thr Glu Thr Ala
                580                 585                 590
```

```
Pro Ala Thr Glu Ser Ala Pro Ala Thr Glu Ser Ser Pro Val Ala Pro
            595                 600                 605

Gly Thr Glu Ser Ser Pro Val Ala Pro Glu Ser Ser Ala Pro Ala Thr
        610                 615                 620

Glu Ser Ala Pro Ala Thr Glu Ser Ser Pro Val Ala Pro Gly Thr Glu
625                 630                 635                 640

Thr Thr Pro Ala Thr Pro Gly Ala Glu Ser Thr Pro Val Ala Pro Val
                645                 650                 655

Ala Pro Glu Ser Ser Ala Pro Ala Val Glu Ser Ser Pro Val Ala Pro
            660                 665                 670

Gly Val Glu Thr Thr Pro Val Ala Pro Val Ala Pro Ser Thr Thr Ala
        675                 680                 685

Lys Thr Ser Ala Leu Val Ser Thr Thr Glu Gly Thr Ile Pro Thr Thr
        690                 695                 700

Leu Glu Ser Val Pro Ala Ile Gln Pro Ser Ala Asn Ser Ser Tyr Thr
705                 710                 715                 720

Ile Ala Ser Val Ser Ser Phe Glu Gly Ala Gly Asn Asn Met Arg Leu
                725                 730                 735

Thr Tyr Gly Ala Ala Ile Ile Gly Leu Ala Ala Phe Leu Ile
            740                 745                 750

<210> SEQ ID NO 5
<211> LENGTH: 43
<212> TYPE: DNA
<213> ORGANISM: Candida albicans

<400> SEQUENCE: 5
ttttgtacaa gctttttttt tttttttttt tttttttttt ttt                43

<210> SEQ ID NO 6
<211> LENGTH: 44
<212> TYPE: DNA
<213> ORGANISM: Candida albicans

<400> SEQUENCE: 6
ctaatacgac tcactatagg gctcgagcgg ccgcccgggc aggt               44

<210> SEQ ID NO 7
<211> LENGTH: 10
<212> TYPE: DNA
<213> ORGANISM: Candida albicans

<400> SEQUENCE: 7
acctgcccgg                                                     10

<210> SEQ ID NO 8
<211> LENGTH: 43
<212> TYPE: DNA
<213> ORGANISM: Candida albicans

<400> SEQUENCE: 8
tgtagcgtga agacgacaga aagggcgtgg tgcggagggc ggt                43

<210> SEQ ID NO 9
<211> LENGTH: 11
<212> TYPE: DNA
<213> ORGANISM: Candida albicans

<400> SEQUENCE: 9
```

```
                    -continued accgccctcc g                                          11

<210> SEQ ID NO 10
<211> LENGTH: 22
<212> TYPE: DNA
<213> ORGANISM: Candida albicans

<400> SEQUENCE: 10
ctaatacgac tcactatagg gc                                    22

<210> SEQ ID NO 11
<211> LENGTH: 21
<212> TYPE: DNA
<213> ORGANISM: Candida albicans

<400> SEQUENCE: 11
tgtagcgtga agacgacaga a                                     21

<210> SEQ ID NO 12
<211> LENGTH: 22
<212> TYPE: DNA
<213> ORGANISM: Candida albicans

<400> SEQUENCE: 12
tcgagcggcc gcccgggcag gt                                    22

<210> SEQ ID NO 13
<211> LENGTH: 22
<212> TYPE: DNA
<213> ORGANISM: Candida albicans

<400> SEQUENCE: 13
agggcgtggt gcggagggcg gt                                    22
```